US009943412B2

(12) United States Patent
Skaer

(10) Patent No.: US 9,943,412 B2
(45) Date of Patent: Apr. 17, 2018

(54) IMPLANTABLE REPAIR DEVICE

(71) Applicant: ORTHOX LIMITED, Abingdon, Oxfordshire (GB)

(72) Inventor: Nicholas Skaer, Abingdon (GB)

(73) Assignee: ORTHOX LIMITED, Abingdon, Oxfordshire (GB)

(*) Notice: Subject to any disclaimer, the term of this patent is extended or adjusted under 35 U.S.C. 154(b) by 66 days.

(21) Appl. No.: 14/351,952

(22) PCT Filed: Oct. 18, 2012

(86) PCT No.: PCT/GB2012/052583
§ 371 (c)(1),
(2) Date: Apr. 15, 2014

(87) PCT Pub. No.: WO2013/057497
PCT Pub. Date: Apr. 25, 2013

(65) Prior Publication Data
US 2014/0277452 A1    Sep. 18, 2014

(30) Foreign Application Priority Data
Oct. 19, 2011 (GB) .................................. 1118000.7

(51) Int. Cl.
*A61L 27/56* (2006.01)
*A61F 2/30* (2006.01)
*A61L 27/22* (2006.01)

(52) U.S. Cl.
CPC ........ *A61F 2/30756* (2013.01); *A61L 27/227* (2013.01); *A61L 27/56* (2013.01); *A61F 2002/30757* (2013.01); *A61L 2430/06* (2013.01)

(58) Field of Classification Search
CPC ............... A61F 2/30756; A61F 2/3603; A61F 2002/30757; A61L 27/3604;
(Continued)

(56) References Cited

U.S. PATENT DOCUMENTS

2009/0171467 A1* 7/2009 Mann et al. ............... 623/23.63
2011/0172394 A1* 7/2011 Knight et al. ................ 530/353
(Continued)

FOREIGN PATENT DOCUMENTS

WO    WO 2007/020449    2/2007
WO    WO 2009/133532    11/2009
(Continued)

Primary Examiner — David Isabella
Assistant Examiner — Rokhaya Diop
(74) Attorney, Agent, or Firm — Notaro, Michalos & Zaccaria P.C.

(57) ABSTRACT

An implantable repair device for the repair, augmentation or replacement of tissue, uses silk fibroin and has a smooth surface and a porous surface. The smooth surface has a measured Sa value of less than approximately 0.1 μm when using Atomic Force Microscopy when samples of the repair device are fully hydrated by imaging through fluid in peak force tapping mode. A method of preparing such an implantable repair device includes preparing a gel from a fibroin solution in a mold, preparing a material by subjecting the gel to one or more steps of freezing and thawing the gel, and creating at least a porous surface on the device, wherein a portion of the mold is adapted to provide at least one smooth surface.

17 Claims, 13 Drawing Sheets

(58) Field of Classification Search
CPC .. A61L 27/3834; A61L 27/3654; A61L 27/54; A61L 27/56; A61L 27/277; A61L 2430/06; A61L 27/227
See application file for complete search history.

(56) References Cited

U.S. PATENT DOCUMENTS

| | | | |
|---|---|---|---|
| 2011/0177151 A1* | 7/2011 | Knight et al. | 424/423 |
| 2013/0172999 A1* | 7/2013 | Kaplan | A61F 2/30756 623/14.12 |

FOREIGN PATENT DOCUMENTS

| | | | |
|---|---|---|---|
| WO | WO 2009/156760 | 12/2009 | |
| WO | WO 2009156226 A2 * | 12/2009 | A61L 27/22 |

* cited by examiner

| FILENAME: | 20 x 20 micron – Figure 12 | 5 x 5 micron - Figure 13 |
|---|---|---|
| AMPLITUDE PARAMETERS | | |
| Sq(um) | 0.060 | 0.048 |
| Ssk | 2.806 | 2.449 |
| Sku | 17.973 | 11.899 |
| Sp(um) | 0.571 | 0.309 |
| Sv(um) | 0.132 | 0.101 |
| Sz(um) | 0.703 | 0.409 |
| SPACING PARAMETERS | | |
| Sds(1/mm^2) | 4585000.000 | 16120000.000 |
| Str | 0.786 | 0.374 |
| Sal(mm) | 0.001 | 0.000 |
| HYBRID PARAMETERS | | |
| Sdq | 0.287 | 0.508 |
| Ssc(1/um) | 5.549 | 17.719 |
| Sdr(%) | 3.981 | 11.507 |
| CURVES PARAMETERS | | |
| Vmp(um^3/mm^2) | 7185.000 | 5813.000 |
| Vmc(um^3/mm^2) | 36190.000 | 29060.000 |
| Vvc(um^3/mm^2) | 64130.000 | 56010.000 |
| Vvv(um^3/mm^2) | 3745.000 | 2423.000 |
| SK FAMILY | | |
| Spk(um) | 0.126 | 0.105 |
| Sk(um) | 0.095 | 0.073 |
| Svk(um) | 0.032 | 0.018 |
| Smr1(%) | 16.500 | 18.400 |
| Smr2(%) | 91.900 | 93.200 |
| OTHER PARAMETERS | | |
| Std(deg) | 0.000 | 0.000 |
| S5z(um) | 0.561 | 0.367 |
| Sa(um) | 0.040 | 0.032 |

FIGURE 15

| FILENAME: | test200001 | test200002 | test200004 | test2000052 |
|---|---|---|---|---|
| AMPLITUDE PARAMETERS | | | | |
| Sq(um) | 0.896 | 0.854 | 0.828 | 0.851 |
| Ssk | 0.087 | -0.016 | 0.21 | 0.272 |
| Sku | 3.528 | 3.305 | 3.401 | 9.67 |
| Sp(um) | 4.661 | 3.596 | 6.244 | 12.973 |
| Sv(um) | 3.342 | 3.406 | 3.253 | 3.724 |
| Sz(um) | 8.003 | 7.002 | 9.497 | 16.698 |
| SPACING PARAMETERS | | | | |
| Sds(1/mm^2) | 1.11E+04 | 1.19E+04 | 1.11E+04 | 1.46E+04 |
| Str | 0.518 | 0.565 | 0.886 | 0.281 |
| Sal(mm) | 0.085 | 0.092 | 0.134 | 0.093 |
| HYBRID PARAMETERS | | | | |
| Sdq | 0.136 | 0.139 | 0.133 | 0.149 |
| Ssc(1/um) | 0.377 | 0.387 | 0.427 | 0.381 |
| Sdr(%) | 1.173 | 1.232 | 1.148 | 1.368 |
| CURVES PARAMETERS | | | | |
| Vmp(um^3/mm^2) | 4.96E+04 | 4.40E+04 | 3.76E+04 | 1.62E+04 |
| Vmc(um^3/mm^2) | 7.73E+05 | 7.40E+05 | 6.90E+05 | 3.80E+05 |
| Vvc(um^3/mm^2) | 1.07E+06 | 1.05E+06 | 1.10E+06 | 4.72E+05 |
| Vvv(um^3/mm^2) | 9.39E+04 | 9.19E+04 | 9.18E+04 | 4.93E+04 |
| SK FAMILY | | | | |
| Spk(um) | 1.01 | 0.904 | 1.019 | 0.856 |
| Sk(um) | 2.384 | 2.238 | 1.828 | 2.318 |
| Svk(um) | 1.065 | 1.034 | 0.849 | 0.935 |
| Smr1(%) | 9 | 9.9 | 15.9 | 6.4 |
| Smr2(%) | 93.1 | 92.5 | 89.6 | 91.1 |
| OTHER PARAMETERS | | | | |
| Std(deg) | 0 | 0 | 0 | 0 |
| S5z(um) | 5.679 | 6.467 | 7.504 | 11.517 |
| Sa(um) | 0.709 | 0.675 | 0.647 | 0.672 |

FIGURE 18

IMPLANTABLE REPAIR DEVICE

BACKGROUND

Technical Field

The present invention relates generally to the field of implantable repair devices. More particularly, but not exclusively, the present invention concerns medical devices for replacing, repairing and/or regenerating damaged or diseased cartilage, and to manufacturing methods for such devices. The present invention more specifically relates to a device for the replacement, partial replacement or augmentation of damaged articular cartilage including, for example, the articular cartilage of the knee joint, the hip joint, the shoulder joint, finger joints and the ankle joint.

Except where specified below the term 'fibroin' is used to refer generically to the main structural protein of cocoon silks whether they are derived from the domesticated Mulberry Silkworm (*Bombyx mori*) or a transgenic silkworm or from any Wild Silkworm including, but not limited to those producing Muga, Eri or Tussah silks. Furthermore, the term 'silk' is used to refer to the natural line fibre that silkworms extrude, which comprises chiefly the two main proteins, sericin and fibroin, fibroin being the structural fibres in the silk, and sericin being the material surrounding the fibroin and sticking the fibres together in the cocoon. 'Silk cocoon' or 'cocoon' is used to refer to the casing of silk spun by the larvae of the silk worm for protection during the pupal stage.

Description of the Related Art

Cartilage in the adult mammalian body occurs in three principal forms: hyaline cartilage; white fibrocartilage; and yellow elastic cartilage. Hyaline cartilage is chiefly present as articular cartilage in the synovial diarthroidal joints e.g. the knee, hip and shoulder, and between long bones, where it forms the stiff and smooth articulating surfaces. White fibrocartilage is present in the menisci of the knee and temporomandibular joint of the jaw and in intervertebral discs. Yellow elastic cartilage gives support to the epiglottis, Eustachian tube and external ear.

Three pathological conditions involving cartilage damage are very common: osteoarthrosis of articular cartilage; injury to the fibrocartilage of the knee menisci; collapse, rupture or herniation of the intervertebral disc; and damage causes by rheumatoid arthritis. Osteoarthrosis is caused by the progressive damage and breakdown of articular cartilage most commonly in the hip and knee and is an important cause of pain and reduced mobility in young and old people alike. Injury to the fibrocartilage of the meniscus is a common sports injury and is also seen as a result of road traffic accidents and other traumatic injuries.

Articular cartilage is highly specialized to provide a relatively frictionless, highly lubricated, wear resistant surface between relatively rigid bones. It also functions to transmit and distribute the forces arising from loaded contact to the surrounding cartilage and underlying subchondral trabecular bone. It is a nonvascular connective tissue largely composed of a fluid phase consisting principally of water and electrolytes interspersed in a solid phase containing type II collagen fibrils, proteo-glycan and other glycoproteins. The latter constituents surround, and are secreted by, highly specialized mesenchymal cells, the chondrocytes, which account for some 10% of the volume of articular cartilage. The collagen fibrils within articular cartilage are arranged in a complex arcade structure forming columns arranged normal to and anchored in the osteochondral junction. These columns run up through the deep layer of cartilage, but the predominant fibre orientation gradually changes to form the arches of the arcade structure in the superficial cartilage. In the superficial layer which abuts the joint space, the meshwork of collagen fibrils is much denser while the fibrils are almost entirely tangential to the cartilage surface. The orientation of collagen in articular cartilage is vital to its mechanical function. Healthy articular cartilage is strong and stiff (modulus between 1 and 20 MPa).

No wholly satisfactory procedure exists for replacing damaged articular cartilage in osteoarthrosis and instead in the case of the two most frequently injured joints, the hip and knee, artificial prostheses are most commonly used to replace the entire joint. While these increase mobility and reduce pain they suffer from progressive wear, mechanical failure, adverse tissue reactions and loosening at their interphase with the bone. Accordingly, there has been much work around the area of providing a suitable implantable repair material with improved performance over the currently available prostheses.

One such device is described in WO 2007/020449 A2, describing a cartilaginous tissue repair device with a biocompatible, bioresorbable three-dimensional silk or other fibre lay and a biocompatible, bioresorbable substantially porous silk-based or other hydrogel partially or substantially filling the interstices of the fibre lay.

International patent application number PCT/IB2009/051775 (published under WO2009/133532 A2) discloses a silk fibroin solution and method that can be used to make an improved fibroin material that has been found to be efficient as an implant for cartilage repair. The method for the preparation of the regenerated silk fibroin solution comprises the steps of: (a) treating the silk or silk with an ionic reagent comprising aqueous solutions of one or more of ammonium hydroxide, ammonium chloride, ammonium bromide, ammonium nitrate, potassium hydroxide, potassium chloride, potassium bromide or potassium nitrate; (b) subsequently drying the silk or silk cocoons after treatment of the silk or silk cocoons with the ionic reagent; and (c) subsequently dissolving the silk or silk cocoons in a chaotropic agent.

Furthermore, International patent application number PCT/GB2009/050727 (published under WO2009/156760 A2) discloses method for the preparation of an implantable material for the repair, augmentation or replacement of bone from a fibroin solution. The method comprises: preparing a gel from fibroin solution; preparing a material by subjecting the gel to one or more steps of freezing and thawing the gel, wherein the step of preparing the gel from the fibroin solution is performed in the presence of phosphate ions. The material is generally treated with calcium ions to form a fibroin-apatite. A further method step comprises the step of treating the material with an isocyanate to form cross-links. The implantable material has been found to be efficient as an implant for bone repair.

It is an object of the present invention to provide an implantable repair device capable of load bearing and with improved or enhanced abilities to integrate with existing bone or cartilage. It is another object of the present invention to provide an implantable repair device adapted to provide improved articulation of the joint following cartilage replacement. It is a further object of the invention to provide a device with a relatively frictionless, highly lubricated, wear resistant surface that minimises damage to juxtaposed tissues and which is as close to the capabilities of articular cartilage as is possible.

SUMMARY OF THE INVENTION

In one aspect of the present invention there is provided an implantable repair device for the repair, augmentation or replacement of tissues, the device comprising silk fibroin and wherein the device comprises a smooth surface and a porous surface.

By "smooth surface", what is meant is a surface that is sufficiently free from irregularities, roughness, or projections so as to have a fine texture, in order that said surface is relatively frictionless and can be lubricated to provide a wear resistant articulation surface for relatively rigid bones or adjacent tissues. To be more specific, a smooth surface is defined as a surface having a measured Sa value of less than approximately 0.1 µm when using Atomic Force Microscopy (using, for example, the Bruker Dimension Icon System), when samples of the repair device are fully hydrated by imaging through fluid in peak force tapping mode. To clarify, above the results are comparable on the analysis of sample sizes of approximately 20 µm×20 µm.

It is envisaged that devices made according to the invention may be used to repair, augment or replace a variety of tissues including, for example, cartilage, bone, vascular tissue, cardiac tissue, gastrointestinal tissue, urinogenital tissue, ligaments and tendons, spinal discs, etc, as well as repair of certain medical indications such as hernias and fistulas.

With this arrangement, the device has a smooth surface that is significantly "smoother" than that required of polymer components in articular replacement surfaces according to BS ISO 7206 part 2 (average roughness of better than 2 µm Ra). Furthermore, the device has a smooth surface that is in the domain of the standard required for spherical articulating surfaces of metallic and ceramic components (Ra values not greater than 0.05 µm and 0.02 µm respectively, using a cut-off value of 0.08 mm when measured in accordance with the principles given in ISO 468:1982). In this respect it is noted that Ra and Sa values both refer to the "Average Roughness" and whilst Ra values are calculated from a single profile trace and Sa values are calculated over an area, the values are loosely comparable.

Accordingly, devices according to the invention have a smooth surface that is durable, relatively frictionless and can be lubricated to provide a wear resistant articulation surface between relatively rigid bones or adjacent tissues. In addition, the porous surface facilitates integration with existing bone or cartilage by providing a surface for aiding ingress of cells and tissue.

Preferably, the smooth surface comprises a Sa value of less than 0.08 µm when measured using Atomic Force Microscopy as above, more preferably, a Sa value of less than 0.06 µm, even more preferably, a Sa value of less than 0.05 µm and most preferably, a Sa value of less than 0.04 µm.

Preferably, the device is formed as a body comprising silk fibroin, said body providing said smooth surface and said porous surface.

Preferably, the smooth surface comprises a surface of a skin. Preferably, a first portion of the body comprises the skin. Preferably, the skin forms the whole of the first portion of the body.

The skin may be between approximately 1 microns and approximately 500 microns thick. Preferably, the skin is between approximately 50 microns and approximately 300 microns thick. More preferably, the skin is between approximately 80 microns and approximately 200 microns thick. Most preferably, the skin is approximately 100 microns thick.

Preferably, the first portion of the body (with the skin having the smooth surface) is formed integrally as part of the body of the device.

Alternatively, the skin may be attached to a pre-formed body. The skin and the pre-formed body may be attached to one another by any suitable method, such as an adhesive.

Alternatively, the skin may be formed in situ on the pre-formed body. For example, the skin may be gelled onto the pre-formed body or pre-formed portion of material that will comprise part of the body.

Preferably, the body further comprises a second portion, the first portion comprising at least the smooth surface and the second portion comprising at least the porous surface. Preferably, therefore, the first portion also comprises the skin. Preferably, the second portion comprises a part of the body in addition to the porous surface.

The first and second portions may each comprise approximately 50% of the volume of the body. Alternatively, the second portion may comprise between approximately 50% and approximately 99% of the volume of the body. Preferably, the second portion comprises approximately 95% of the volume of the body. Most preferably, therefore, the second portion comprises the porous surface and a further part and the first portion comprises the skin and the smooth surface. Preferably, the first and second portions are formed integrally.

Alternatively, the first and second portions may comprise discrete first and second layers, respectively that are fixed to one another. First and second layers may be attached by any suitable method, such as attaching pre-formed layers using an adhesive, or by forming one layer on a pre-formed layer. In the latter scenario, preferably, the first layer is formed on a pre-formed second layer. For example, the smooth surface and/or the skin may be gelled onto a pre-formed layer.

At least one of the first and second layers may comprise a porous surface adapted to facilitate attachment of the two layers. Where one layer is pre-formed, only the pre-formed layer may provide such a surface. Preferably, where both layers are pre-formed, both the first and second layer comprise a porous surface adapted to facilitate attachment to one another.

The second portion (or layer) of the device may partially or completely comprise a bone material, or an implantable bone bio-material.

By "bone material" or "bone bio-material" we mean any suitable material, including autograft, allograft or demineralised bone, calcium phosphate based materials, other mineral composites, polymer-mineral composites, porous bone bio-materials or a material made by the method such as that disclosed in WO2009/156760 A2, namely made by the method comprising the steps of: preparing a gel from a silk fibroin solution; preparing a material by subjecting the gel to one or more steps of freezing and thawing the gel, wherein the step of preparing the gel from the silk fibroin solution is performed in the presence of phosphate ions and the material is further treated with calcium ions to form a fibroin-apatite. The bone materials may have been treated with an isocyanate.

With the material of WO 2009/156760, the fibroin solution may be dispersed with phosphate ions before the step of preparing the gel from the fibroin solution. Preferably, the step of preparing the gel from the fibroin solution comprises a gelling reagent containing phosphate ions. Particularly good results have been observed when the fibroin solution is gelled using an aqueous buffered solution of dihydrogen sodium phosphate adjusted to an alkaline pH. Particularly good results have been obtained where the treatment with the cross-linking agent is carried out with substantially no fibroin swelling agents, such as water, dimethylsulphoxide or dimethylformamide.

Preferably, the body, or the layers or portions forming the body, comprise a regenerated silk fibroin.

By "regenerated silk fibroin" we mean silk fibroin made from a regenerated silk fibroin solution, such as that disclosed in WO2009/133,532 A2, namely a regenerated silk fibroin solution made by the method comprising the steps of: (a) treating the silk or silk cocoons with an ionic reagent comprising aqueous solutions of one or more of ammonium hydroxide, ammonium chloride, ammonium bromide, ammonium nitrate, potassium hydroxide, potassium chloride, potassium bromide or potassium nitrate; (b) subsequently drying the silk or silk cocoons after treatment of the silk or silk cocoons with the ionic reagent; and (c) subsequently dissolving the silk or silk cocoons in a chaotropic agent.

Preferably, at least a part of the body is porous. Preferably, at least a part of the second portion of the body (adjacent to the porous surface) is porous. More preferably, therefore, the porous layer is a continuation of the porous portion of the body. Most preferably, substantially all of the second portion of the body is porous (e.g. not the smooth surface and/or skin).

The pores may range from approximately 10 μm to approximately 1000 μm in diameter. The average pore diameter may range from approximately 100 μm to approximately 500 μm, more particularly, approximately 200 μm to approximately 400 μm. The average pore size may be approximately 300 μm.

The porous part, portion or layer of the body may comprise between approximately 10% and approximately 95% porosity by volume. Preferably, the body comprises between approximately 60% and approximately 95% porosity by volume. More preferably, the body comprises between approximately 70% and approximately 95% porosity by volume. Most preferably, the body comprises approximately 85% porosity by volume.

Preferably, the porous part, portion or layer of the body comprises a substantial proportion of "open pores", with the majority of pores communicating with the porous surface and each pore forming a branched structure of channels, as opposed to "closed pores" which form separate discrete voids.

The open pores may form approximately more than 70% of all pores by volume, preferably, approximately more than 80% of all pores by volume, more preferably, approximately more than 95% of all pores by volume and most preferably, approximately more than 99% of all pores by volume.

The porous surface may be mineralised. The body may be selectively mineralised. By "selectively mineralised" we mean selected areas of the body are mineralised. Most preferably, the second portion or second layer of the body, including the porous surface is mineralised. The first portion or first layer of the body may also be mineralised, but not including the skin or the smooth surface.

Preferably, the selected areas of the body are mineralised with calcium phosphate, most preferably, with hydroxyapatite. Preferably, the hydroxyapatite is present as a nanocomposite throughout the selected porous areas of the body.

Alternatively, calcium phosphate crystals may be nucleated onto the porous surface. Alternatively, still, calcium phosphate crystals may be nucleated onto the porous surface and throughout the selected areas of the body.

Alternatively, the selected areas of the body are mineralised with granules of hydroxyapatite or calcium phosphate. The granules may be attached using an adhesive or cast into the body/lower layer of the body.

The granules may be approximately 0.2 mm to approximately 2 mm in diameter. Preferably, the granules are approximately 0.3 mm to approximately 1.5 mm in diameter. The granules may be between approximately 0.3 mm and approximately 0.7 mm in diameter, or between approximately 0.7 mm and 1.5 mm in diameter. Additionally or alternatively, some or all of the granules may be provided as small as 140 μm in diameter.

The device may comprise a biocompatible fibres or fibre lay.

The fibre lay may be three-dimensional. The fibre lay may be at least partially infiltrated by the gel. The fibre lay may comprise wound or woven or twisted or knitted or braided or stitched or embroidered fibres, or compressed felts, or combined layers of cloth. The fibre lay may be a mesh. Preferably, any fibre lay comprises silk fibroin. The fibre lay may be substantially biomimetic of the fibre pattern of a cartilaginous tissue to be repaired.

The fibres or the fibre lay may be partially dissolved in the body of the device, such that outer layers of the fibres substantially blend or merge into the body of the device. This forms a stronger bond with the body of the device increasing strength of the device.

Preferably, the device is provided as a 'thin' component in the range of approximately 0.2 mm to approximately 6 mm thick suitable for use in resurfacing procedures.

Alternatively, the device may be provided as a 'thick' component in the range of approximately 6 mm to approximately 10 mm thick suitable for use in replacement procedures.

The device may be shaped to mimic the shape and contours of the cartilage component that it is intended to replace. For example, a disc may be provided for resurfacing operations, whereas a contoured device may be provided for replacement procedures.

Additionally, or alternatively, the device may be flexible to be adapted to comprise the contours of the cartilage component and/or the bone component on which it is to sit.

In use, the device may be attached in vivo using pins, tacks, nails, darts, arrows, barbs, adhesive or sutures/stitches.

In another aspect of the invention therefore, there is provided a method of preparing an implantable repair device or a portion or layer of such a device for the repair, augmentation or replacement of cartilage, the method comprising the steps of: preparing a gel from a fibroin solution in a mould; preparing a material by subjecting the gel to one or more steps of freezing and thawing the gel; and creating a porous surface on said device, wherein in preparing the gel from the fibroin solution, a portion of the mould is adapted to provide at least one smooth surface on said gel.

By "mould" we mean the vessel in which the fibroin solution and subsequent gel is contained.

Preferably, creating a porous surface on said device comprises the step of removing at least a portion of a surface of the device to expose the pores thereunder. Preferably, therefore, substantially all of the mould is adapted to provide smooth surfaces on the gel.

Preferably, removal of the surface includes cutting away the said surface from the gel. Any suitable method may be used to expose the porous surface, such as shaving, abrading, or dissolving away said surface.

Alternatively, the mould may be adapted to provide the porous surface. In this case, approximately 50% of the mould may be adapted to provide a smooth surface(s) on the gel and approximately 50% of the mould may be adapted to provide porous surface(s) on the gel. Alternatively, approximately 60% of the mould may be adapted to provide a smooth surface and in other applications approximately 20% of the mould may be adapted to provide a smooth surface.

A part of the mould may be polished.

Preferably, at least a part of the mould comprises a dialysis membrane, dialysis bag, dialysis vessel or dialysis surface and the silk fibroin solution is gelled against the dialysis membrane, bag, vessel or surface in order to achieve a skin with the smooth surface. The method may use a dialysis membrane, bag, vessel or surface comprising a cellulose acetate dialysis membrane.

Alternatively, the silk fibroin solution may be gelled against a glass surface or other smooth surface.

Alternatively, the method may comprise subjecting the device to post-forming processing in order to achieve a smooth surface.

Preferably, the silk fibroin solution is gelled by treating the fibroin solution with an aqueous solution of one or more gelling reagents, such as, for example, an acid. By way of example, particularly good results have been achieved using a gelling agent comprising an acetic acid solution. The regenerated silk fibroin solution may be gelled to form a hydrogel. Gelation may be performed at a temperature of approximately 20° C. using a 1% solution of acetic acid for a period of time determined by the depth of penetration of the gelation required. For example, with a device approximately 8 mm thick, gelation time may be between approximately two and eight hours, more preferably, four to six hours.

Any mould may be removed prior to freezing and thawing steps. Preferably, the freezing (but not necessary the thawing steps) are conducted with any mould in place.

Freezing of the gel may be performed at any suitable temperature, for example, within a temperature range of approximately −1° C. to approximately −120° C. Preferably, freezing is performed within a temperature range of approximately −10° C. to approximately −30° C. More preferably, freezing is performed within a temperature range of approximately −14° C. to approximately −20° C. For example, good results have been achieved where freezing is performed at a temperature of approximately −14° C. to −18° C.

A plurality of freezing and thawing cycles may be performed to increase the diameters of the pores.

The method may provide a portion or layer of an implantable device. Preferably, however, the method comprises forming the device as an integrated device with said smooth surface and said porous surface integral to one another. Preferably, the smooth surface is formed as part of a skin that is substantially free of pores or at least comprises pores in the order of less than approximately 1 μm.

Alternatively, the method may comprise pre-forming a first layer comprising a skin and the smooth surface and pre-forming a second layer comprising the porous surface and attaching the two parts. The method may comprise attaching the pre-formed layers to one another by any suitable method, such as an adhesive.

In another alternative, the method may comprise pre-forming a skin and pre-forming a body and attaching the two parts. The method may comprise attaching the pre-formed skin and the pre-formed body to one another by any suitable method, such as an adhesive.

In a further alternative, the method may comprise pre-forming a body and forming the smooth surface and skin onto the pre-formed body. The method may therefore, comprise gelling a silk fibroin solution onto the pre-formed body, in which case, the smooth surface may be obtained by forming a silk fibroin solution according to any of the previously described methods against a mould adapted to provide said smooth surface, or subjecting a surface of the gel to post-forming processing.

The method may comprise forming the body, or pre-formed layers or skin from a regenerated fibroin solution, such as that disclosed in WO2009/133532 A2 and discussed in detail above.

When using a regenerated fibroin solution, the silk or silk cocoons may be degummed (removing the sericin) either before or after or consecutively with the treatment with the ionic reagent. Degumming may use a proteolytic enzyme that selectively leaves sericin, but not fibroin, such as trypsin. The dissolving of silk in a chaotropic agent may be a chaotropic agent of up to 9.4M and/or for a period of time of time of less than 24 hours, more preferably using an agent of between approximately 8.0M and 9.4M, even more preferably, at 37° C. Most preferably, dissolving of silk in a chaotropic agent may comprise a solution of approximately 8.25M to 9.0M, again, preferably at 37° C. Good results have been achieved at 37° C., 8.5M of chaotropic agent concentration and less than 12 hours of time. Preferably, the chaotropic agent is lithium bromide.

Preferably, the method comprises the steps in the following order: (a) dialysis of a regenerated fibroin solution to remove a chaotropic agent; (b) freezing the dialysed regenerated fibroin solution in a mould; (c) removal of the mould (d) simultaneous thawing and gelling of the dialysed regenerated fibroin solution; and (c) subjecting the gel to one or more freeze/thaw cycles.

Prior to step (a), preferably, individual fibres or a fibre lay are/is introduced to the regenerated fibroin solution with the chaotropic agent for a specified period prior to commencing dialysis of the regenerated fibroin solution. Where the individual fibres/fibre lay comprises fibroin, or another material which is soluble in the chaotropic agent, this has the effect of introducing a controlled/partial dissolution of the introduced fibres/fibre lay. The dissolution is halted by commencing removal of the chaotropic agent during dialysis. This is considered beneficial as it serves to integrate the undissolved individual fibres/fibre lay with the regenerated fibroin solution, resulting in a continuum between the individual fibres/fibre lay and the rest of the body of the device following subsequent processing steps. Integration of the individual fibres/fibre lay and the rest of the body of the device may provide improved mechanical properties and/or improved resistance to delamination of the individual fibres/fibre lay from the rest of the body of the device.

Dialysis against pure water may be used to remove the chaotropic agent and the solution may be concentrated to approximately 5-25% w/v. Preferably, during dialysis, the regenerated fibroin solution and the dialysate should be agitated at a "gentle shake". Preferably during dialysis, the dialysate is tested for chaotropic agent. The test may comprise a silver nitrate test performed on the dialysate. Preferably however, the test comprises checking the conductivity of the dialysate. Preferably, therefore, the test comprises use of a conductivity/electrolysis meter, which is placed in the dialysate. Preferably, the dialysis of the regenerated fibroin solution may be concluded when the conductivity reading is less than or approximately equal to 500 μS/cm (micro Siemens per cm), more preferably, 100 μS/cm and most preferably, 50 μS/cm. In the event that a conductivity reading is recorded outside of the chosen readings, the regenerated fibroin solution can be subject to further dialysis, although it is appreciated that a higher conductivity may be tolerated. Testing of the amount of chaotropic agent in the dialysate provides a direct indication of how much chaotropic agent remains in the fibroin solution.

In step (b), the freezing helps to retain the shape of the solution in the shape of the mould, prior to step (c).

Preferably, step (d) comprises gelling in the conditions above. By thawing during gelling, the shape of the mould is retained.

Step (e) introduces pores into the gel.

The method may comprise incorporating biocompatible fibres or fibre lay in the device. The method may therefore, comprise forming the fibre lay by winding or weaving or twisting or knitting or braiding or stitching or embroiding fibres, or compressing felts or combining layers of cloth. The fibre lay may be formed so as to be substantially biomimetic of the fibre pattern of a cartilaginous tissue to be repaired.

The method may comprise at least partially infiltrating the fibre layer with the gel. Therefore, the method may comprise the additional step of positioning the fibre lay in the mould with the fibroin solution.

Preferably, the method comprises adding the fibres or fibre lay to the solution prior to dialysis.

Preferably, the fibres or fibre lay are/is partially dissolved in the solution before gelling the solution around the fibres/fibre lay. This allows outer layers of the fibres to substantially blend or merge with the fibroin matrix there around in the final body of the device.

Preferably, any fibre lay comprises silk fibroin.

The method may comprise the step of mineralising at least the porous surface. Preferably, therefore, the method comprises the step of forming said porous surface and then selectively mineralising at least the porous surface.

Preferably, the method comprises subsequently treating at least the porous surface of the gel with calcium ions to form a hydroxyapatite nanocomposite on at least said porous surface. Most preferably, at least a second portion or second layer of the gel is treated with calcium ions to form a hydroxyapatite nanocomposite in said second portion or second layer. The method may employ steps of partially submersing the gel with at least the porous surface in a calcium ion solution or by dipping consecutively in solutions containing first phosphate and then calcium ions. A barrier means may be used in order to prevent calcium ions from migrating through the gel beyond a predetermined point.

By "barrier means", we mean, for example, the incorporation or application of a thin polymeric barrier layer or a barrier formed by selective freezing of an upper portion or layer of the gel or an ion exclusion membrane between an upper and lower portion or layer of the gel.

The method may comprise an implantable bio-material, as the pre-formed lower layer or pre-formed body such as that disclosed in WO2009/156760 A2 and discussed above.

Alternatively, the method may comprise the step of nucleating calcium phosphate crystals on to at least the porous surface. The method may employ steps of partially submersing the gel with at least the porous surface in a calcium phosphate solution or by dipping consecutively in solutions containing first phosphate and then calcium ions. A barrier means (as above) may be used in order to prevent the solution from migrating through the gel beyond a predetermined point.

Alternatively still, the method may comprise the step of including mineral granules on said porous surface. The method may comprise the step of casting at least a surface of the second portion or second layer on a bed of said granules. The bed of granules may be loosely attached to a support surface, or otherwise temporarily fixed to the support surface. Alternatively, the method may comprise the step of attaching said granules to the porous surface post-formation of said porous surface, using for example, a fixative, such as an adhesive.

It will be appreciated that the preferred features described in relation to each of the above aspects of the invention apply to all other aspects of the invention.

BRIEF DESCRIPTION OF THE DRAWINGS

For a better understanding of the invention, and to show how exemplary embodiments may be carried into effect, reference will now be made to the accompanying drawings in which:

FIG. 8 is an image demonstrating the flexibility of the other implantable repair device of FIG. 3a;

FIG. 9 is an alternative image demonstrating the flexibility of the implantable repair device of FIG. 3a;

FIG. 15 shows the 3D surface Texture Parameters of FIGS. 12 and 13;

FIG. 18 shows the 3D surface Texture Parameters of FIGS. 16 and 17;

DETAILED DESCRIPTION OF THE EXEMPLARY EMBODIMENTS

Figure 10:
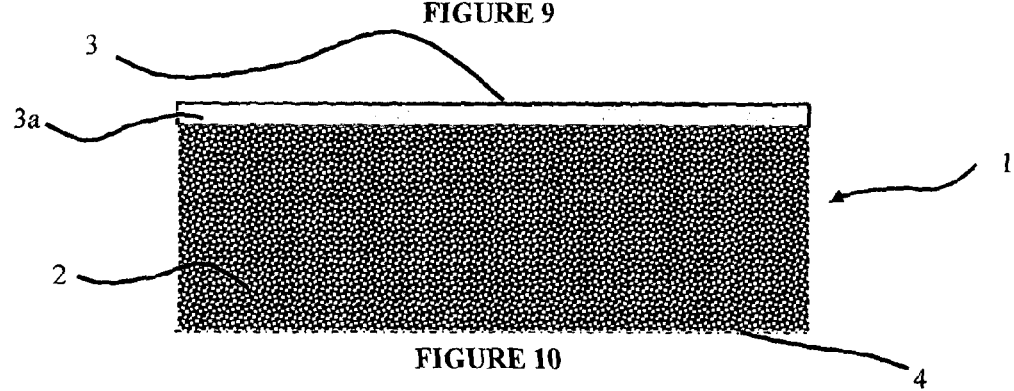
FIG. 10 is a diagram showing an implantable repair device according to another embodiment of the present invention.

As can be seen particularly in FIG. 10, an implantable repair device 1 for the repair, augmentation or replacement of articular cartilage comprises a body 2 with a smooth surface 3 and a porous surface 4.

Figure 1:
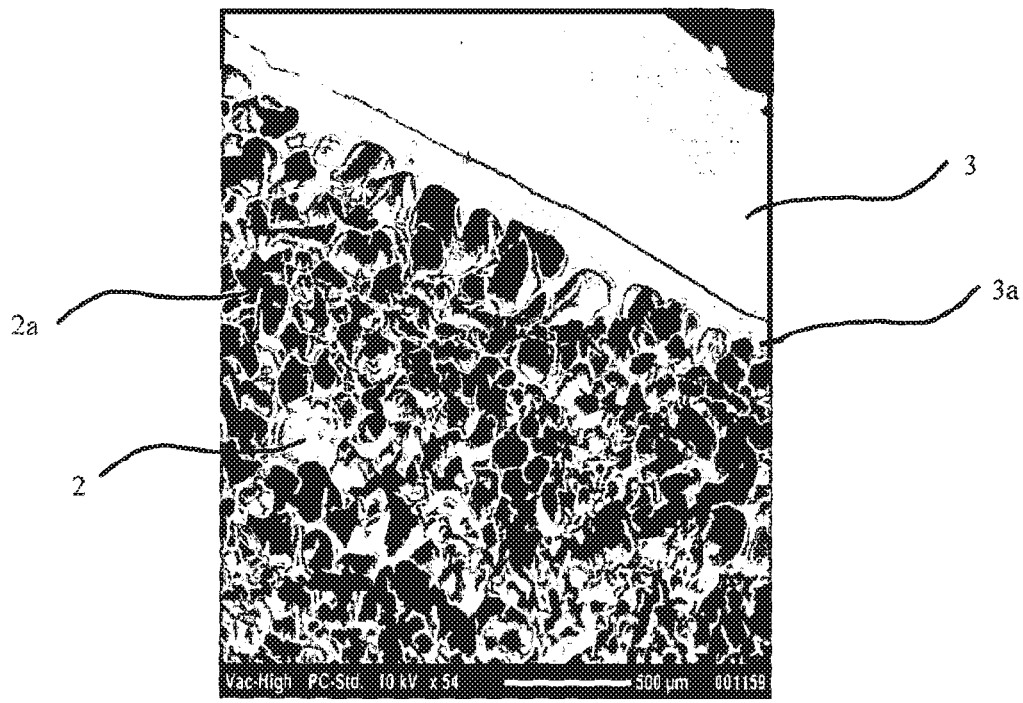
FIG. 1 is a scanning electron microscope (SEM) image (×54 magnification) of a smooth surface and porous body of a section of an implantable repair device according to an exemplary embodiment of the present invention.
Figure 2:
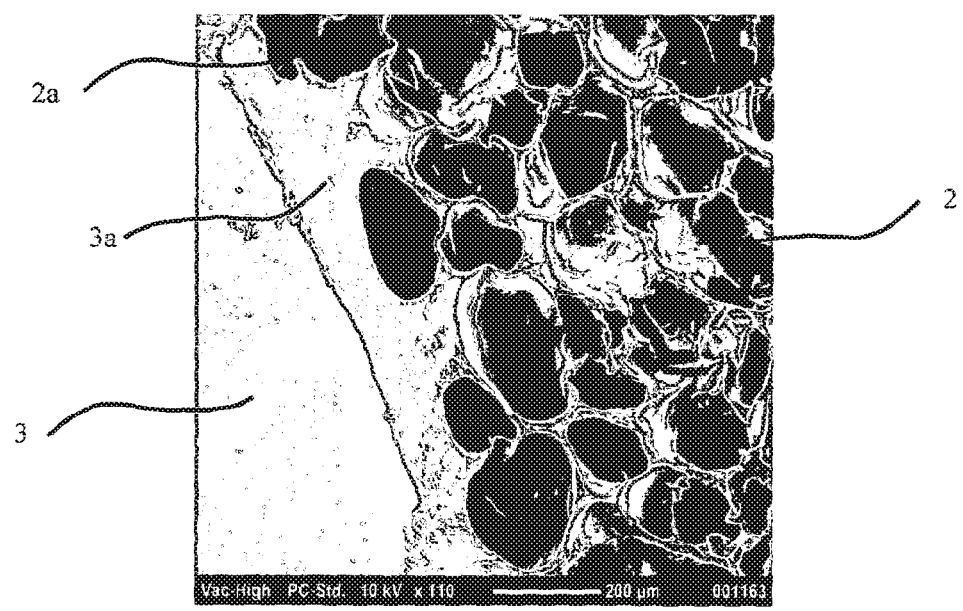
FIG. 2 is a scanning electron microscope (SEM) image (×110 magnification) of a portion of the device shown in FIG. 1.

In one embodiment, substantially the whole of the body 2 of the device 1 is porous. The pores 2a can be seen in detail in the electron micrographs of FIGS. 1 and 2, where the body 2 has a porosity of approximately at least 85%. In addition, approximately at least 95% of the pores 2a are "open" pores, i.e. the majority of the pores communicate with the porous surface and each pore appears to branch into its own network of channels 2a deep into the body 2. This is as opposed to pores that provide independent and/or closed voids distributed throughout the body 2.

Some of the branched pores may bisect other pores. A network between the pores may be augmented using a laser or drill, or other device to create holes.

The smooth surface 3 is approximately 50 microns thick and can be seen to be fully integrated with the porous body 2 as part of (the surface of) a substantially non-porous skin 3a. When the smooth surface 3/skin 3a is formed integrally with the porous body 2, the risk of delamination of the body 2 from the surface 31 skin 3a is reduced.

The porous surface 4 is a continuation of the porous body 2.

Figure 3A:
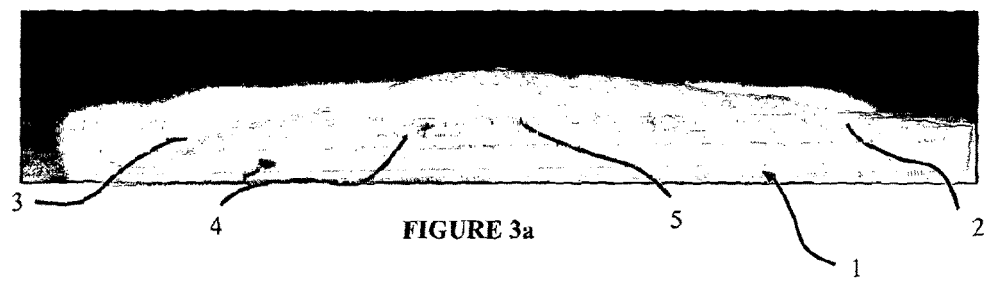
FIG. 3a is a side view image showing a smooth upper surface and a granule (small size) embedded lower surface of an implantable repair device made according to an embodiment of the present invention.
Figure 3B:
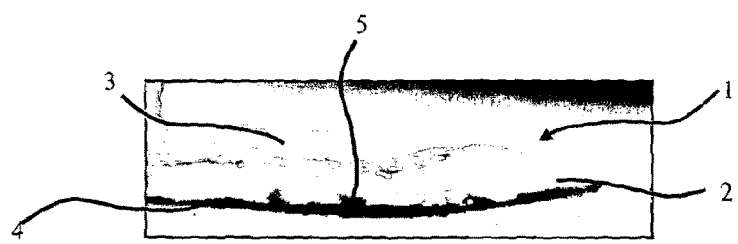
FIG. 3b is a side view image showing a smooth upper surface and a granule (large size) embedded lower surface of another implantable repair device made according to another embodiment of the present invention.
Figure 4:
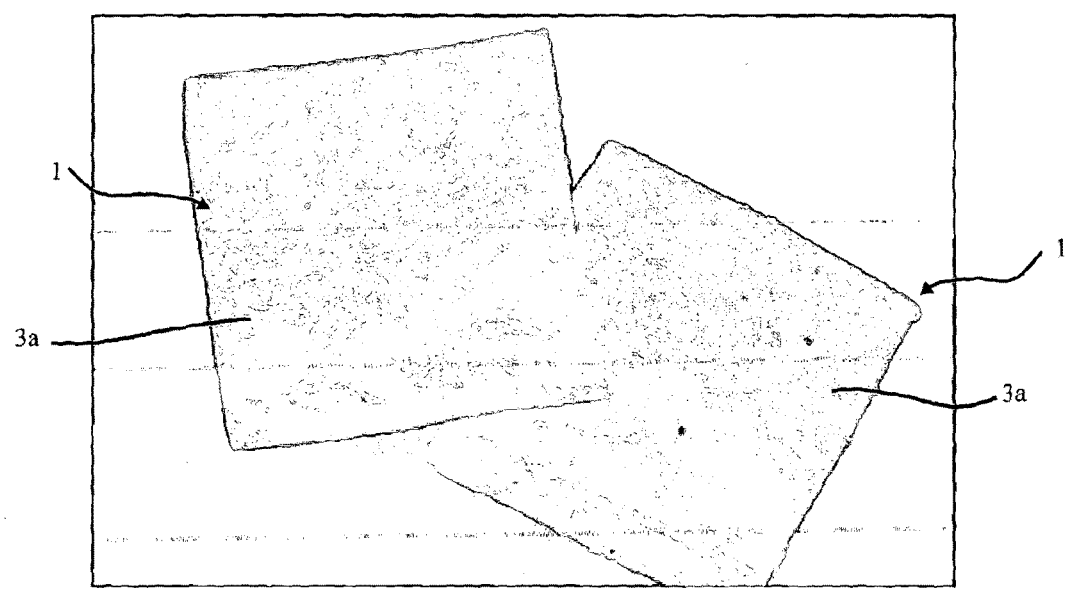
FIG. 4 is an image showing the smooth upper surfaces of the two implantable repair devices of FIGS. 3a and 3b.
Figure 5:
FIG. 5 is an image showing the granule embedded lower surfaces of the two implantable repair devices of FIGS. 3a and 3b.
Figure 6:
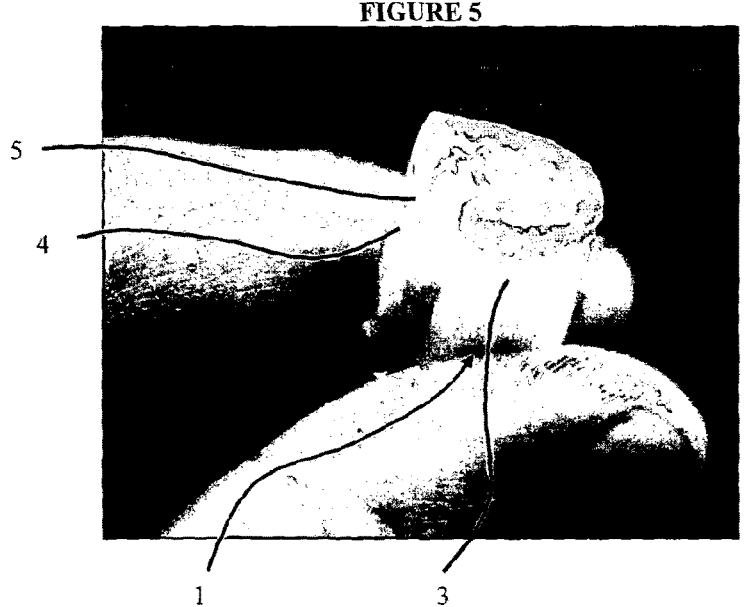
FIG. 6 is an image demonstrating the flexibility of the implantable repair device of FIG. 3b.
Figure 7:
FIG. 7 is an alternative image demonstrating the flexibility of the implantable repair device of FIG. 3b.
Figure 8:
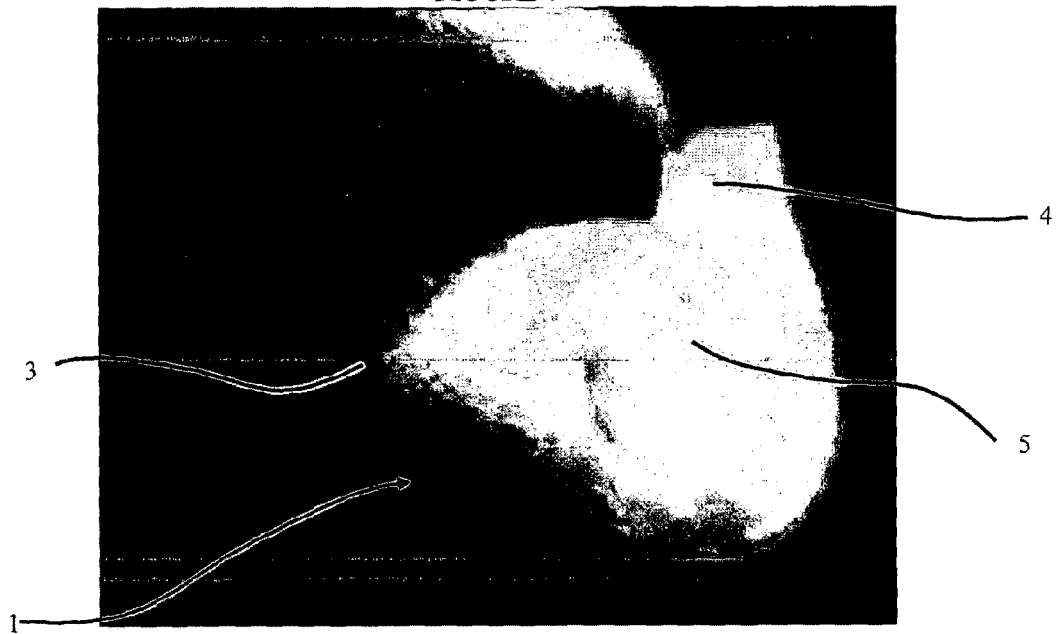
Figure 9:

It can be seen from two different embodiments of the device 1 in FIGS. 3a and 3b, that the porous surface 4 is mineralised using calcium phosphate granules 5, which are embedded in the porous surface 4 and into the porous body of the device 1. The size of the granules 5 can be varied and in FIG. 3a (plus FIGS. 8 and 9), the granules 5 are approximately 0.3 mm in diameter on average, whereas in FIG. 3b (plus FIGS. 6 and 7), the granules 5 are approximately 1 mm in diameter on average.

In an alternative and preferred embodiment (FIG. 10), a porous mineralised architecture has a high content of calcium phosphate crystallites that cover the walls of the pores in the form of a hydroxyapatite nanocomposite.

Figure 11:
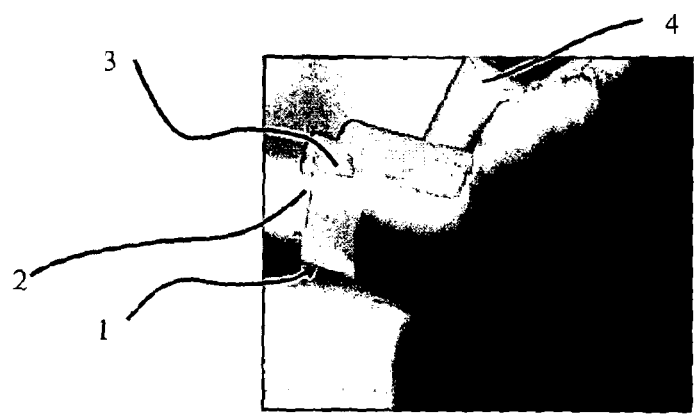
FIG. 11 is an image showing a smooth upper surface and a porous lower surface of another implantable repair device made according to another embodiment of the present invention.

In a further preferred embodiment (FIG. 11), the porous surface is not mineralised.

Figure 19:
FIG. 19 shows an example of a meniscal repair device according to an embodiment of the invention incorporating a fibre lay, and FIGS. 20a/b show a section through a sub-cutaneous implantation in a rat with a device according to an embodiment of the invention incorporating a fibre lay.

A further alternative embodiment is shown in FIG. 19. This shows a meniscus repair device 1. A fibre lay 6 is clearly integrated with the porous body 2. The smooth surface 3 can be seen.

Characteristics of the Implantable Repair Devices

The smooth surface of the devices aid articulation, whereas the porous surface facilitates integration of the device in situ. In addition, the flexibility of the device as a thin component means that the device may be rolled up to be introduced arthroscopically.

The porous, biocompatible, largely pyrogen-free, implantable device described above is highly advantageous, because it combines the properties of compressive strength, compressive elastic modulus and compressive toughness close to that of previously defined target values and excellent tissue regenerative properties. These properties make the device suitable for all immediate and non-immediate load-bearing applications and non-load-bearing applications.

The similarity of the mechanical properties of the implantable device to those of natural bone and cartilage make the material capable of immediately bearing the stresses to which bones and cartilage are subjected in normal movement, thereby avoiding the need for prolonged periods of bed rest and minimizing the use of internal or external supports. The implantable material can therefore, be used in load-bearing implant locations to replace all or a part of a natural component.

The high and open porosity and suitable mean pore size of the implantable material enables cells, nutrients, tissues, fluids and developing capillaries, for example, to migrate into the device encouraging deposition of new musculoskeletal, or other, tissues. This together with the excellent biocompatibility of the implantable material allows cells to grow and differentiate within the pores of the device enabling the rapid de novo production of natural tissues.

Overview of the Method for Making Implantable Repair Devices According to the Invention Preparation of a Regenerated Silk Fibroin Solution Silk or silk cocoons are treated with ammonia or with an aqueous solution containing ammonium ions.

Treatment of the silk with ammonia gas, or a dilute solution of ammonia or an ammonium salt greatly increased the readiness of silk to dissolve in a lithium bromide solution or other chaotropic agent. In this step, it is believed that ammonium ions act as a 'salting in' reagent, which increases the subsequent solubility of the protein in the chaotropic reagent by assisting in the removal of an inner water shell surrounding the protein chains and by binding to the charged amino acid side chains of the fibroin. This treatment has been found to be effective when applied directly to undegummed cocoons, to raw silk fibres, or to degummed or partially degummed silk whether degummed by conventional industrial degumming methods or by enzymatic degumming. Ammonia or ammonium ions were also effective when included as a component of the buffer used for enzymic degumming. Therefore, treatment with ammonia or ammonium enables a range of milder treatments in which the temperature, concentration of the chaotropic agent or time required for solution can be varied singly or in combination. These milder treatments resulted in more rapid gelling times for the fibroin solution and stronger stiffer materials at the end of the process. It is currently considered that other pairs of ions with the same size, for example, potassium chloride will also have the same effect and could be used in place of the ammonia. This is supported by two lines of evidence: (1) The Jones-Dole viscosity (a measure of the chaotropicity) of potassium and chloride ions are similar as is the charge density enabling the ions to form ion pairs and help to remove an inner water shell of the protein (properties shared with ammonium chloride; and (2) Potassium chloride has been used to "salt in" proteins at salt concentrations generally ranging from 50 mM to 600 mM. Suitable ionic reagents may include aqueous solutions of ammonium hydroxide, ammonium chloride, ammonium bromide, ammonium nitrate, potassium hydroxide, potassium chloride, potassium bromide, potassium nitrate, rubidium hydroxide, rubidium chloride, rubidium bromide and rubidium nitrate.

The silk or silk cocoons are degummed under mild conditions by selectively removing the sericin. This is done by enzymatically cutting and removing the sericin using a suitable enzyme which cleaves sericin, but produces little or no cleavage of fibroin.

The choice of the degumming method has been found to be crucial for the gelling time of the fibroin and stiffness and strength of the final material. Commercial reeling and degumming processes both use temperatures of around 100° C. and the use of sodium carbonate and/or Marscille's soap and it was found that reeled raw silks and degummed silks dissolved less readily than cocoon silks probably as a consequence of this treatment. Degumming with commercial alcalase (bacterial subtilisin) enabled the degumming temperature to be reduced to 60° C. Alcalase is a member of the Serine S8 endoproteinase family and is likely to degrade fibroins badly as it has a broad specificity with a preference for a large uncharged residue in the P1 position. *B. mori* and *Antheraea pernyi* heavy chain fibroins have many predicted cleavage sites for this enzyme. The susceptibility of *B. mori* fibroin to alcalase cleavage was confirmed by polyacrylamide gel electrophoresis of a regenerated fibroin solution prepared from alcalase degummed silk. In the case of degumming using trypsin the temperature for degumming could be reduced to 20° C. to 40° C. and gave gels with reduced gelling times, and with improved stiffness and strength compared with conventional high temperature degumming procedures. In contrast to alcalase, the tool PeptideCleaver showed few predicted trypsin cleavage sites in the consensus sequence of the repetitive crystalline domains and of the hydrophilic spacers of *B. mori* fibroin heavy chain fibroin and none in the consensus sequence or hydrophilic spacer in *A. pernyi* heavy chain fibroin. This suggested that it might be beneficial to degum silks in trypsin for the preparation of regenerated fibroin solutions. Trypsin was indeed found to be highly advantageous for degumming silk for the formation of improved regenerated fibroin solutions. Silks degummed with trypsin gave regenerated silk solutions with shorter gelation times and capable of forming stiffer gels than those obtained from regenerated silk prepared from silk degummed with alcalase. Degumming with trypsin gave gelling times of less than 5 minutes on exposure to one gelling agent, glacial acetic acid vapour and also gave the stiffest and strongest materials suggesting that trypsin under these conditions produced much less chain cleavage than alcalase treatment. It will be understood that other proteolytic enzymes producing little or no cleavage of fibroin may also be advantageous for degumming silks for the preparation of improved regenerated fibroin solutions. The observation that *B. mori* heavy chain fibroin contains very little proline while this amino acid is relatively abundant in sericin suggested that proline endopeptidase would be an ideal candidate to selectively remove sericin while producing little or no damage to fibroin. It is considered that it may be of further advantage to use cocoon or raw silks degummed with trypsin in ammonium carbonate buffer at 40° C.

The silk or silk cocoons are dried by extracting water.

The silk or silk cocoons are dissolved in an aqueous lithium bromide (chaotropic agent) solution at one or more of a temperature of less than 60° C. and/or with a concentration of lithium bromide solution of less than 9.5M and/or for a period of time of less than 24 hours.

The chaotropic agents are removed by dialysis using ultrapure water in the temperature range of approximately 4-50° C. The fibroin solution can be concentrated.

It was found to be highly beneficial to dialyse regenerated fibroin solutions against type I milliQ water (available from Millipore, 290 Concord Road, Billerica, Mass. 01821, US), otherwise known as ultrapure water, to remove the chaotropic agent from the silk solution. It was noted that PIPES or Tris buffers or impurities in deionised water adversely affected the stiffness and strength of the final product when used as dialysants. It was noted that the inclusion of PIPES or Tris buffers or impurities in the dialysant also increased the viscosity of the regenerated silk solution, probably as a result of their ability to encourage the aggregation of the fibroin chains by binding to them. This is thought to be disadvantageous in the formation of strong and stiff fibroin gels.

A. Preparation of an Integral Device from the Regenerated Silk Fibroin Solution

The dialysis bag/membrane containing the fibroin solution is placed in a shaped vessel and the dialysis bag is clamped at both ends to obtain the required shape of the device. This causes the bag to stretch to the shape of the mould which is advantageous and removes the need to transfer the bag to a mould afterwards, which can cause wrinkling of the membrane. Alternatively, the solution is transferred to a mould with a polished surface/a surface adapted to provide a smooth surface on the body.

It has been found to be advantageous to gel 8-10% w/v optimised regenerated fibroin solution prepared from trypsin degummed silk contained in dialysis vessels shaped to create a 8 mm deep component for up to 6 hours at room temperature in 1% acetic acid. In the dialysis bag, the solution is gelled.

It has been found that freezing under-gelled fibroin resulted in a reduction in the pore size and a weaker material while strong over-gelation gave non-porous gels containing a low density of large splits produced by large ice crystals. It was found that the length of exposure and concentration of the buffer or vapour required for optimal gelation depended on the geometry and size of the fibroin cast. Thus longer treatments were required to optimally gel fibroin in moulds constructed from 20 mm diameter dialysis tubing compared with 10 mm dialysis tubes.

The gel is subjected to one (or maybe more) freezing cycles. Each freezing cycle comprises a freezing step and a thawing step. By freezing the gel the water droplets are turned to ice crystals which form pockets or pores within the gel. Subjecting the gel to one or more freezing cycles may introduce a greater degree of open pores.

Freezing is thought to result in phase separation of a fibroin-rich phase from a fibroin-poor phase and ice crystal formation in the latter. These two mechanisms are thought to combine to give rise to a high density of open pores in the gel. The freezing step also makes the fibroin in the pore walls insoluble in water and most other aqueous solvents suggesting that it has been partially converted to the insoluble silk II state in which intra- and inter-molecularly bonded beta-sheets predominate. This transition to the silk II state may result from the removal of water from the protein chains produced by a combination of phase separation and their alignment and pulling together, both as a consequence of ice crystal formation. Thus the formation of the insoluble silk II state rather closely mimics the natural process by which silks are extruded, from the silk worm which also depends on phase separation, loss of water from the fibroin-rich phase and strain dependent orientation and silk II formation. For a single freezing cycle, the temperature of the freezing step has an effect on the pore size with the largest pores produced by freezing between −12° C. to −18° C. Varying the temperature and including low concentrations of antifreezes or sugars in the regenerated protein solution can be used to vary the ice crystal size and morphology and hence the size and shape of the pores in the material. Increasing the number of freezing cycles produced an increase in the size of the pores as a result of damage by ice crystals. This was accompanied by some loss in the stiffness and strength of the final material. It will be understood that methods other than gelation and freezing can be used to introduce open pores into the optimised regenerated fibroin solution. By way of example only these include salt leaching and gas foaming.

Other elements can be incorporated into the fibroin solution before gelation, including, for example, fibre lays, short staple fibres, filler particles, drugs, antineoplastic drugs, antibiotics, other biopolymers and other active principles. In particular, fibres are often incorporated at the start of the dialysis step, although fibres can be incorporated into the body at almost any step prior to gelation.

The material is immersed in an aqueous solution of ethanol to partially dehydrated and facilitate the formation of the silk II (beta sheet) form of the fibroin.

Treating the material with an aqueous ethanol solution after freezing is thought to facilitate the formation of the silk II (beta sheet) inter- and intra-molecular hydrogen bonds, which improves the mechanical stability of the gel and increases insolubility and resistance to enzymatic attack.

The material is rehydrated in distilled water or saline and may be cut open to expose the pores in the body on the intended porous surface.

The material can, in some instances include the additional step of crosslinking the fibroin using an undiluted isocyanate or a highly concentrated isocyanate solution in dimethylsulphoxide or other organic solvent, in which case excess isocyanate (and solvent) is subsequently removed. This step can be introduced between the ethanoic washing and rehydration.

B. Preparation of an Integral Device from the Regenerated Silk Fibroin Solution with a Hydroxyapatite Nanocomposite The fibroin solution is gelled as above in Preparation Method A, whilst introducing phosphate ions into the fibroin solution by treating the solution with a concentrated buffered solution containing phosphate ions. In the preferred embodiment, the buffered phosphate solution comprises dihydrogen sodium phosphate buffered with 2-amino-2-(hydroxymethyl)propane-1,3-diol (Tris) buffer, adjusted to an alkaline pH. The concentration of the dihydrogen sodium phosphate was 0.9 M in 1% Tris buffer and adjusted to pH 9.0.

The concentration of the dihydrogen sodium phosphate and the length of exposure of the material to it are crucial to the pore size and the strength and stiffness of the resulting gel. It has been discovered that by gelling the solution in the presence of phosphate ions allowed the phosphate ions to disperse throughout the solution and therefore, be integrated into the gel. This facilitates the formation of the fibroin-apatite nanocomposite when calcium ions are added at a later stage. It was found that if the gel was subsequently treated with phosphate ions, an apatite coating was achieved when calcium ions were added at a later stage. Although the preferred embodiment combines introducing phosphate ions and gelling the fibroin solution in a single step, other gelling agents or methods can be used to gel the fibroin solution before introducing the phosphate ions, including by way of example only, heat, microwave radiation, ultrasound treatment, laser radiation, acidic solutions and acidic vapours.

The fibroin gel is treated with a concentrated buffered solution containing calcium ions to form a fibroin-apatite material. The apatite is present as a nanocomposite in and on the walls of the pores. The buffered calcium solution comprises calcium chloride also buffered with Tris to an alkaline pH.

The calcium ions form an apatite with the phosphate ions. If phosphate ions are dispersed throughout the fibroin solution prior to gelling, then a fibroin-apatite nanocomposite is achieved. However, if the fibroin solution is first gelled and then treated with phosphate ions, an apatite coating is observed, but not a nanocomposite. The use of calcium chloride induces some chloride substitution of the apatite. This is desirable as it is thought to speed resorption of the apatite compared with unsubstituted hydroxyapatite. A further embodiment uses calcium nitrate solution in place of calcium chloride solution, which avoids the presence of chloride ions in the apatite and results in the formation of a pure hydroxyapatite rather than a partially chloride-substituted hydroxyapatite (i.e. a part chlorapatite, part hydroxyapatite). The material is treated with calcium ions at a basic pH, which avoids the formation of an acidic or amorphous apatite. Good results have been achieved when the material is treated with calcium ions at a pH of approximately 9.0.

After partially dehydrating in ethanol, as much free water as possible is removed from the material, by for example, vacuum drying, or by ethanoic dehydration.

The fibroin in the material is optionally cross-linked using an undiluted isocyanate or a highly concentrated isocyanate solution in dimethylsulphoxide or other organic solvent.

Cross-linking increases the stiffness of the implantable repair device and increases the resistance of the device to enzymatic attack thereby slowing resorption. It was found that if a swelling agent was used, this caused the fibroin to swell, which resulted in a separation of the apatite from the fibroin. Consequently, this caused the material to have reduced stiffness, which is turn resulted in a tendency of the material to flex and cause the apatite to 'flake' out of the material. It was also found that varying the length of exposure of the fibroin-apatite to an isocyanate cross-linking agent could be used to tune the density of covalent cross-linking and hence the stiffness of the implantable repair device. It was also found that varying the density of covalent cross-linking could be used to vary the resistance of the fibroin gel to enzymatic attack and thereby extend the resorption time in a controlled way. Attempts to cross-link the fibroin in the material with solutions of 20% hexamethylene di-isocyanate in dimethylsulphoxide (DMSO) using the published protocol described by Arai, T, Ishikawa, H., Freddi, Winkler, G S and Tsukada, M (2001) op.cit., did not produce satisfactory implantable repair device. In the published protocol, it is through that, because swelling of the fibroin-apatite in the DMSO resulted in a separation of the mineral from the fibroin. Therefore, the method uses an isocyanate cross-linking agent in the absence of water or other swelling agents such as dimethylsulphoxide.

Excess isocyanate is removed by treating the material with a dry solvent.

Isocyanate cross-linking does not appear to interfere with the biocompatibility of the material provided that excess cross-linking agent is removed by thorough washing. This was established in vitro by growing human stromal cells on and in the porous fibroin-apatite composite and in vivo after subcutaneous implantation into mice.

The mineralisation provides load-bearing properties like that of existing human bone.

C. Preparation of an Integral Device with a Hydroxyapatite Nanocomposite Portion The method above is adapted such that only a second portion of the gel device, with the porous surface and not the smooth surface is exposed to the calcium ions, to form the hydroxyapatite. This is achieved in one of two ways.

In one method, the porous surface and a second portion adjacent to the porous surface is submerged in calcium ion solution, such that a first portion with the smooth surface is not exposed to the calcium ions (partial submergence). The first portion and smooth surface do not therefore, form a hydroxyapatite using the calcium ions.

In a second embodiment, which may be used in isolation or in addition to partial submergence, a barrier means is provided between a first portion with the smooth surface and a second portion adjacent to the porous surface. The barrier means may include any suitable means for preventing calcium ions from either getting into the first portion and/or preventing the calcium ions from interacting with the phosphate ions.

D. Preparation of a Laminate Device with a Hydroxyapatite Nanocomposite or Other Bone Biomaterial A first layer without mineralisation, i.e. not being gelled in the presence of phosphate ions and subsequently not having been exposed to calcium ions or being cross-linked, is provided on a second layer that has been pre-formed.

In one method, the second layer is formed, mineralised and cross-linked using the method A above, without any consideration for developing a smooth surface. Alternatively, any suitable bone material may be used as the second layer. The second layer is placed in a mould adapted to provide a smooth surface e.g. a dialysis membrane. The first layer is gelled in situ on the second layer in the absence of phosphate ions and is then subjected to the freezing (and potentially thawing) steps to provide pores in the first layer, partially dehydrated in ethanol and rehydrated as described above. The first layer is not mineralised.

In a second method, the first layer is pre-formed with pores, but without exposure to phosphate ions. The first layer with pores is fixed/adhered to a hydroxyapatite nanocomposite second layer that has been pre-formed. Alternatively, any suitable bone material may be used as the second layer. A suitable adhesive can be used to fix the two layers together.

In a third method a second layer is pre-formed as a gel having been exposed to phosphate ions. The second gel layer is transferred to a mould adapted to provide a smooth surface. The first layer is gelled onto the second gel layer in the absence of phosphate ions. The two layers are subjected to the freezing and thawing steps together. Calcium ions are introduced as described above. When the calcium ions are introduced, the calcium ions only form the hydroxyapatite nanocomposite with the phosphate ions in the second layer and so the first layer is not mineralised.

E. Preparation of a Device with a Mineralised Porous Surface

The fibroin solution is transferred to a mould and is gelled as before in Preparation method A. The gel is subjected to one or more freezing cycles as before. The calcium phosphate granules are applied to the porous surface of the device during the process in one of two ways.

In one method, the fibroin solution is gelled onto a bed of calcium phosphate (or other suitable bone biomaterials, such as bio ceramic, bio glass, or calcium sulphate granules, such that the granules are embedded in the body and present a face at the porous surface of the gel.

In another method, the gel may be cut open to expose the pores and the granules embedded in the body on the intended porous surface.

In an alternative method, the calcium phosphate (or other suitable bone biomaterials, such as bio ceramics, bio glass or calcium sulphate granules) are fixed to the porous surface using a suitable adhesive.

In any of the above embodiments, fibres or a fibre lay can also be utilised. The fibres or fibre lay can be placed inside the dialysis bag. If a silk fibroin fibre lay is employed then the filled bag can be left for a period to allow the surface of the silk fibroin fibres to partially dissolve. This is beneficial as it allows a continuous silk fibroin fibre-matrix composite to form when the device is gelled, which improves the overall strength of the device. The fibre lay can be made of degummed mulberry silk fibroin fibres.

In one method, the fibre lay can be placed inside the dialysis bag, approximately dividing the bag into upper and lower portions. The interstices of the fibre lay are small enough to prevent the granules from passing through the fibre lay. A mixture of silk fibroin (with or without the chaotropic agent) and granules is placed in the lower portion of the divided dialysis bag, and silk fibroin (with or without the chaotropic agent) is placed in the upper portion of the dialysis bag. The bag and the fibre lay are clamped at both ends of the bag, holding the fibre lay in position longitudinally through the dialysis bag and segregating the granules to the lower portion of the device. The device is then dialysed, gelled, frozen (as described above) and hardened (by ethanoic dehydration), the dialysis bag removed and a lower surface is removed from the device to expose the porous surface and embedded granules.

Alternatively, the granules are placed between two pieces of the above described fibre lay to a thickness of several granules depth. The fibre lays with the granules sandwiched between them are then placed longitudinally into a dialysis hag and the bag and fibre lays clamped to both close the hag and hold the fibre lays and sandwiched granules so they run centrally through the bag. The bag is then filled with a fibroin solution (with or without chaotropic agent), the fibre lays and bag clamped at the other end, and the whole is then placed in a shaped vessel and left for a period to allow the surface of the fibre lays to be dissolved as above (but not so long as to permit the structure of the fibre lays to be compromised). The whole is then dialysed, gelled and frozen (as described above) and hardened (by ethanoic dehydration), and the dialysis bag removed. Following this, the gel is cut longitudinally through the centre of the granules such that the granules and internal fibroin porosity is exposed. This gives two approximately identical devices, each with a smooth surface (which was juxtaposed to the dialysis bag) and a porous, granule embedded surface.

In any of the above, a plurality of fibre lays may be employed to increase the structural strength of the resultant device.

Overview of the Method of Implantation of the Implantable Repair Device

In a preferred embodiment, the device is implanted in vivo without it first being seeded with tissue cultured cells, but with the porous surface adjacent to a patient's bone or cartilage surface and the smooth surface disposed in a position suitable for receiving an articulating member.

Alternatively, the device can be seeded immediately prior to implantation with autologous or allogeneic tissue cultured cells or blood, bone marrow, platelet-rich plasma or cells harvested from the patient shortly before implantation.

By way of example only, such tissue cultured cells include bone marrow stromal cells, mesenchymal stem cells, an osteogenic cell line, or chondrocytes. As a further alternative, the device can be seeded with cells and then subjected to tissue culture with or without applied cyclical strain, to accelerate the formation of tissue in the device before implantation.

The size and shape of the device can be varied for different applications. Thus anatomically-shaped devices can be produced by casting the material in a suitably shaped mould or by grinding, cutting or otherwise machining a larger block of material. Alternatively, discs can be produced by casting or machining or a combination of these processes for resurfacing applications. The material can also be shaped in theatre using a scalpel or other tool to enable the implant to be approximated to the desired space or cavity into which it is to be fitted.

SPECIFIC METHODS OF SELECT EMBODIMENTS

Example 1:—Protocol for the Preparation of Optimised Regenerated Fibroin Solution from Reeled Raw Silk or Silk Cocoons and Preparation of an Integral Implantable Repair Device from Optimised Regenerated Fibroin Solution Silk Supply Raw Mulberry Silk Fibre (*Bombyx mori*) is used. The preferred specification is Brazilian origin, 20/22 denier, single skeins, on hank, not more than two years old. The preferred silk supplier is Silk Opportunities Ltd.

Figure 12A:
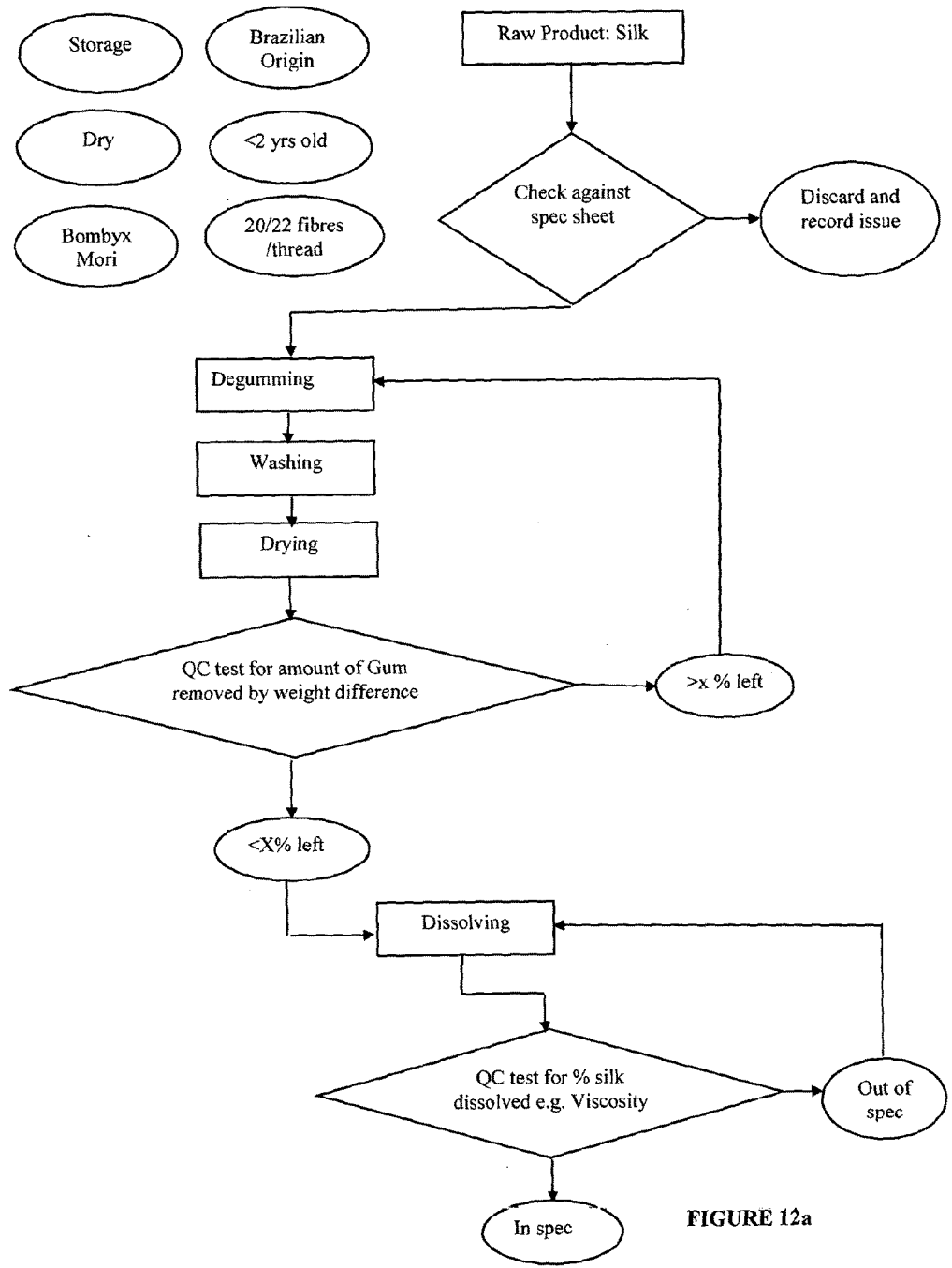
FIGS. 12a/b are flow charts showing the method steps for making an implantable repair device according to the invention.

Degumming (FIG. 12a)
7.11 g of Ammonium bicarbonate
6.75 g EDTA
0.18 g porcine trypsin
1.8 g Tween-20 solution
Milli Q/Elix grade 1 water (15-18.2 MΩ·cm resistivity at 25° C.)
60 g silk 1. Take silk skein and cut away the string tying silk together. Discard string.
2. Cut skein into +/−5 cm pieces and spread them open in bag.
3. Weigh out 60 g of cut silk pieces in a 4.6 l box.
4. Take 600 ml glass beaker and a plastic weighing boat; weigh into the boat EDTA, ammonium bicarbonate and Tween-20; add it and 600 ml MilliQ/Elix water to glass beaker: use magnetic stirrer mix until dissolved.
5. Once solution is dissolved take Trypsin from freezer and weigh.
6. Add trypsin to the 600 ml of water containing EDTA, Ammonium bicarbonate and Tween-20; stir manually until dissolved.
7. Add the 600 ml solution from step 6 to the box of silk pieces; add further 1200 ml MilliQ/Elix water.
8. Stir silk pieces in solution until thoroughly wet.
9. Seal 4.6 l boxes and put into shaker incubator.
10. Set incubator timer for 4 hours at 37 C, 150 rpm.
11. After 4 hours drain solution through a sieve to separate the degummed silk (fibroin) pieces.

Washing/Drying (FIG. 12a)
Degummed fibroin pieces from step 11
2 ml Tween-20
MilliQ/Elix grade 1 water (15-18.2 MΩ·cm resistivity at 25° C.)
Tap water 12. Run tap water through sieve for 5 minutes to wash fibroin pieces.
13. Put silk pieces into 1.5 l watertight plastic tub and add 1 l tap water with 2 ml Tween-20.
14. Shake thoroughly by hand and leave for 5 minutes.
15. Drain fibroin pieces through a sieve.
16. Run tap water through sieve for 5 minutes to wash fibroin pieces.
17. Put fibroin pieces into washing machine.
18. Add 5 l warm tap water. Run 15 minute wash cycle with machine on 'drain' setting.
19. Repeat step 18 a further three times.
20. Add 5 l MilliQ/Elix water. Run 15 minute wash cycle with machine on 'drain' setting.
21. Repeat step 20 a further three times.
22. Transfer fibroin pieces to spin side of washing tub.
23. Spin for 5 minutes.
24. Remove fibroin pieces from washing tub and spread out on paper towel to air dry overnight.
25. If the fibroin weigh less than 45 g it is dry enough to proceed to step 26. If fibroin weigh more than 45 g use vacuum oven to dry further. To do this place fibroin pieces in oven. Close door and lock. Switch vacuum pump on, close top valve on oven, open bottom valve on oven, switch cold trap on, close the lid on cold trap, check whether gauge on oven reaches 1000 mBar. Leave for 1 hour.

Fibroin may be kept for up to a week at room temperature at this stage.

Dissolving (FIG. 12a)
Degummed, washed and dried fibroin from step 3
369.09 g Lithium Bromide (LiBr)
MilliQ/Elix grade 1 water (15-18.2 MΩ·cm resistivity at 25° C.)

26. To make LiBr solution: weigh 369.09 g g LiBr and pour it gently into 300 ml MilliQ/Elix water in a 500 ml beaker whilst magnetically stirring (caution: exothermic reaction). Once dissolved, pour into 500 ml measuring Erlenmeyer and top up to 500 ml line with MilliQ/Elix water to achieve a 8.5M solution.
27. Multiply the weight of fibroin from step 25 by a factor of five to give the quantity (in ml) of LiBr required.
28. Put fibroin into 1 l bottle and add measured LiBr solution calculated from step 26. Stopper bottle and put into shaker incubator, into a bottle holder.
29. Program incubator to 37° C., at 200 rpm for 10 hours, then revert to 10° C., at 75 rpm (standard procedure would be to start dissolving process at 4 pm and remove from incubator at 10 am next day to fit into normal working hours).
30. Proceed directly to step 31. Alternatively dissolved fibroin/LiBr solution may be stored in fridge at 4° C. for 1 day.

Figure 12B:
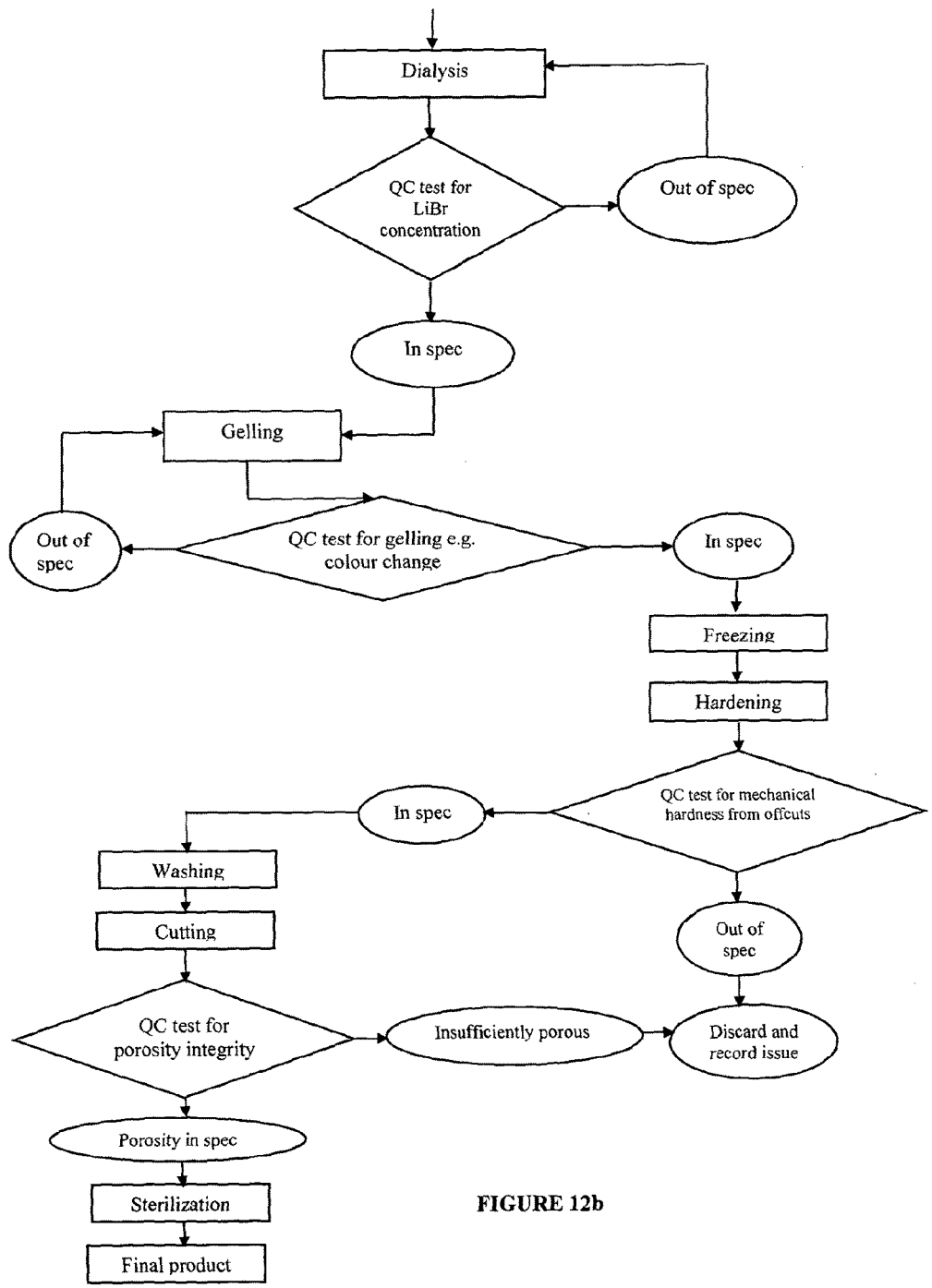

Dialysis (FIG. 12b)
Dissolved fibroin/LiBr solution from step 30
MilliQ/Elix grade 1 water (15-18.2 MΩ·cm resistivity at 25° C.)

31. Sieve dissolved fibroin/LiBr through a plastic sieve into a 600 ml beaker.
32. Cut 25 cm long lengths dialysis membrane and allow softening in water for more than 5 min, running MilliQ/Elix water through membrane to rinse inside.
33. Tie a knot at one end of the softened membrane.

34. Place a clamp on the membrane next to and above the knot.
35. Tighten clamp closure by repeatedly looping an elastic band around the non-hinge end of the clamp.
36. Fix a 1 cm plastic cylinder on the other end of the membrane using a looped elastic band to hold open the membrane making it easier to pour fibroin/LiBr solution into the membrane.
37. Place the softened membrane symmetrically along the middle of the mould lower and smooth out wrinkles.
38. Place the mould upper in place and screw the mould together sandwiching the membrane (with 4 screws and 4 wingnuts).
39. Pour fibroin/LiBr solution into syringes, allow air bubbles to collect at top and remove air.
40. Inject 15 ml LiBr/fibroin solution in membrane, remove air-bubbles, and clamp with a second clamp allowing no air to be trapped in the clamped membrane. Secure clamp with an elastic band, wash out the end of the membrane with running water and tie a knot close to the second clamp.
41. Place 1 mould per 4.6l box and add 3l MilliQ/Elix water. Seal Box.
42. Leave for 2 hours at Room temp. Empty and refresh with 3l MilliQ/Elix water. Seal Box.
43. Leave overnight and next day repeat in morning and evening with 3l MilliQ/Elix water.
44. Leave overnight and refresh in morning with 3l MilliQ water (18.2 MΩ·cm resistivity at 25° C., Millipore Integral 5 unit)
   Through steps 42-44, in many cases the box should be continuously agitated at a "gentle shake".
45. Leave until afternoon and then test if LiBr remains in the dialysate:
46. Take 0.5 ml dialysate and add 0.5 ml 1% silver nitrate in 1.5 ml eppendorf
47. Cap, shake and leave for 30 mins in ambient natural light (e.g. windowsill).
48. Black precipitation shows there's still LiBr and further dialysis is required.
49. Refresh 4.6l box with 3l MilliQ water and leave overnight.
   Alternatively, to steps 46-49, the test for remaining LiBr in the regenerated fibroin solution may utilise a conducting/electrolysis meter, which is placed in the solution. If a conductivity of greater than or equal to 50 µS/cm (micro Siemens per cm) is measured, the solution can be subject to further dialysis, although it is appreciated that a higher conductivity may be tolerated.
50. Repeat dialysis until dialysate is acceptably clear of LiBr.
51. Remove moulds from LiBr-free dialysate water and put into freezer for a minimum 4 hours or until frozen through.
   Gelling (FIG. 12b)
Fibroin solution in clamped membranes in secured moulds from step 51
Glacial (100%) Acetic acid
MilliQ water (18.2 MΩ·cm resistivity at 25° C.)
52. Remove the moulds from the frozen membrane and fibroin solution.
53. Fill a 4.6l box with 1.5l MilliQ water.
54. Add 15 ml acetic acid to give 1% solution of acetic acid.
55. Place the frozen membrane and fibroin solution horizontally in 1% acetic acid (two per box). Time 2 min. apart to give time to close the moulds afterwards. Seal box.
56. Leave 2 hours in the acetic acid solution.
57. Remove from acetic acid solution and place back in mould. Secure moulds with screws and wingnuts.
58. Proceed directly to step 59.
   Freezing (FIG. 12b)
Fibroin gel in clamped membranes in secured moulds from step 58
59. Place fibroin gel in clamped membranes in secured moulds from step 58 in freezer.
60. Freeze for at least 2 days at −18 C (can be stored at this stage indeterminately).
61. Moulds can be removed for reuse after 12 hours.
   Hardening (FIG. 12b)
Frozen fibroin gel in clamped membranes in secured moulds from step 61
100% Ethanol
MilliQ water (18.2 MΩ·cm resistivity at 25° C.)
62. Fill 4.6l box with 1l MilliQ water
63. Add 1 l 100% ethanol to give a 50% solution.
64. Remove the moulds and clamps from the frozen fibroin gel devices in membranes.
65. Place up to 8 frozen fibroin gel devices in membranes per box in the 50% ethanol.
66. Seal box and leave at room temperature for 2 days.
   Washing (FIG. 12b)
Hardened fibroin gel in membranes from step 66
MilliQ water (18.2 MΩ·cm resistivity at 25° C.)
67. Fill 4.6l box with 3l MilliQ water.
68. Take hardened fibroin gel in membranes out of ethanol and place in MilliQ water in 4.6l box. Seal box.
69. Discard water after 24 hours and refresh with 3l MilliQ water.
70. Repeat step 69 a further two times.
   Cutting
71. Using a clean razor blade cut away dialysis membrane and one smooth surface of the device to expose the porous body. Discard dialysis membrane and smooth offcut.

Example 2:—First Protocol for the Preparation of an Integral Implantable Repair Device from Optimised Fibroin Solution with a Mineralised Surface 1. An aqueous 10% w/v *Bombyx mori* optimized regenerated fibroin solution was prepared as described in Example 1.
2. Granules of a porous bone material (in combination with polymers both natural and synthetic, growth factors, cells or other biologics), which are between 100 microns and 3 mm in average diameter, were mixed with the solution from step 1. In practice, the granules can be mixed with the fibroin solution at any point following step 29/30 of Example 1 but prior to dialysis of the solution in step 41.
3. The mixture was placed in a Visking bag (molecular weight cut-off 12-14 kDa) of required dimensions.
4. The Visking bag was placed in a shaped vessel of the appropriate size and shape (e.g. two flat smooth surfaces held apart by spacers to give a flat device of the required thickness) and the bag was clamped closed at both ends.
5. The mould was placed horizontally such that the granules settled to the bottom of the Visking bag under gravity (care is subsequently taken not to disturb this arrangement in subsequent processing).
6. The mixture was dialysed for a minimum of five hours and a maximum of three days against ultrapure water at between 5° C. and 30° C. with or without constant stirring in covered beakers—a large excess of ultrapure water was changed at least five times at evenly spaced intervals;

7. After dialysis the regenerated fibroin solution was either:
   i. Frozen to maintain the shape of the fibroin solution in the dialysis membrane and the mould then removed, or;
   ii. The non-porous mould removed and replaced with a mould of the same shape and sufficiently porous to permit free ingress of the gelation agent used in step 55 of Example 1.
8. After dialysis the regenerated fibroin solution was gelled in the bags with aqueous 1% w/v acetic acid at 20° C. for an optimal time which depended on the size of the Visking bag.
9. Samples of the resultant gel from step 8 of this Example were transferred to a freezer bath for 24 hours at −13° C. to introduce pores into the material.
10. The samples were placed in 50% ethanol for two days to convert the protein into the Silk II state.
11. The samples were rehydrated using saline or ultrapure water for two days.
12. The dialysis membrane was removed from the device and at the same time, the granule containing surface of the device was cut or shaved to abrade away or dissolve away the surface and expose the pores.

Example 3:—Second Protocol for the Preparation of an Integral Implantable Repair Device from Optimised Fibroin Solution with a Mineralised Surface 1. An aqueous 10% w/v *Bombyx mori* optimized regenerated fibroin solution was prepared as described in Example 1;
2. Granules of a porous bone replacement material (BRM), bone substitute material (BSM), or bone graft material (BGM) formed, for example, from calcium phosphate, bio glass, bio ceramic, calcium sulphate (any of the above in combination with polymers both natural and synthetic, growth factors, cells or other biologics), which are between 100 microns and 3 mm in average diameter, were placed on a surface of a flat plate of stainless steel or other inert material and glued to the plate with Poly(4-vinyl pyridene) adhesive, although any other suitable adhesive (that will subsequently dissolve away) can be used.
3. The plate was placed inside a Visking bag large enough to accommodate it and the bag was filled up with the fibroin solution (at any point following step 29/30 of Example 1 but prior to dialysis of the solution in step 41).
4. The bag was placed in a shaped vessel with the plate at the bottom of the Visking bag.
5. The mixture was dialysed for a minimum of five hours and a maximum of three days against ultrapure water at between 5° C. and 30° C. with or without constant stirring in covered beakers—a large excess of ultrapure water was changed at least five times at evenly spaced intervals;
6. After dialysis the regenerated fibroin solution was either:
   i. Frozen to maintain the shape of the fibroin solution in the dialysis membrane and the mould then removed, or;
   ii. The non-porous mould removed and replaced with a mould of the same shape and sufficiently porous to permit free ingress of the gelation agent used in step 55 of Example 1.
7. After dialysis the regenerated fibroin solution was gelled in the bags with aqueous 1% w/v acetic acid at 20° C. for an optimal time which depended on the size of the Visking bag.
8. Samples of the resultant gel from step 7 of this Example were transferred to a freezer bath for 24 hours at −13° C. to introduce pores into the material.
9. The samples were placed in 50% ethanol for two days to convert the protein into the Silk II state.
10. The dialysis membrane was removed from the device and the steel plate removed.
11. The samples were rehydrated using saline or ultrapure water for two days.
12. The granule containing surface of the device was cut or shaved to abrade away or dissolve away the surface and expose the pores.

Implantation Studies

A one month pilot study for any toxic effects of fibres in a sub-cut model in two rats was conducted. A Rat NPIMR sub-cutaneous implantation is shown in FIG. 20*a* and in close up in FIG. 20*b*.

Figure 20A:
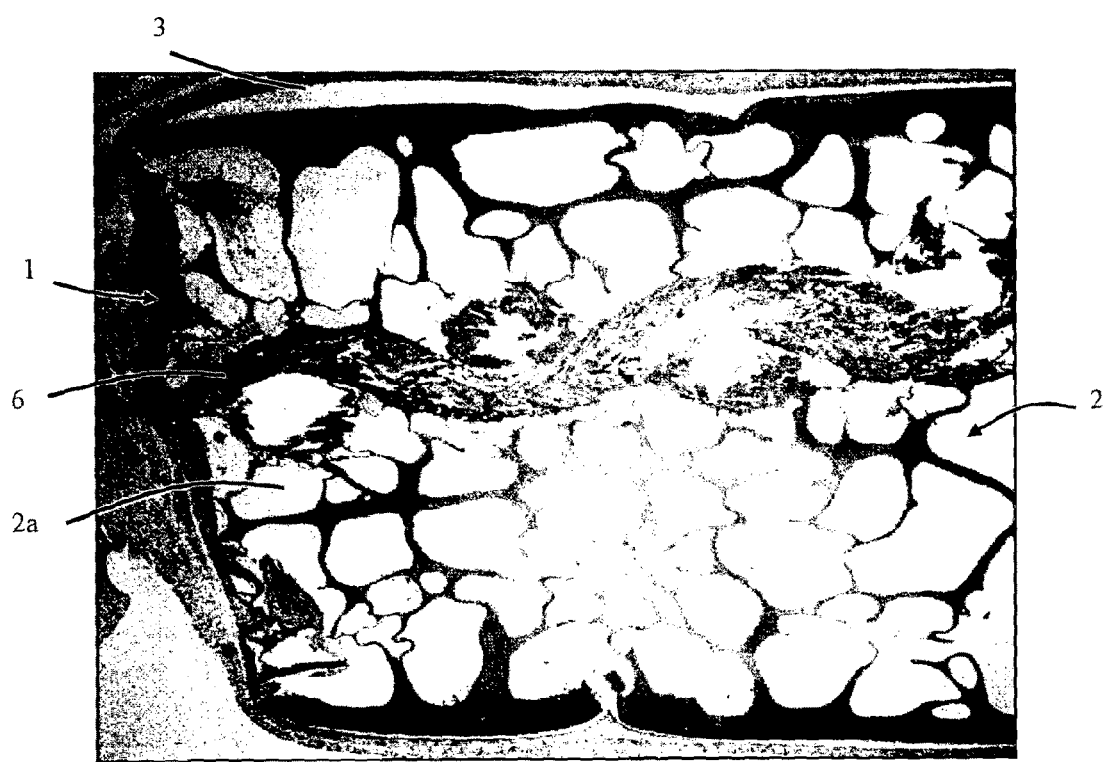
Figure 20B:

FIG. 20*a* shows very clearly the pores 2*a* in the porous body 2 of the device 1 and the smooth surface 3. A cross-section through a fibre 6 can also be seen. In FIG. 20*b*, an example of the result of partial dissolution of the fibres can be seen, where a fibre 6 forms a continuum with the surrounding body 2 of the device. This blended interface between the fibres 6 and the body 2, is thought to increase the strength of the material and reduce the chance of any delamination with any partially dissolved fibres or a fibre lay.

The studies showed no aberrant in-life behaviour or clinical observations and the samples were well tolerated. Minimal fibrous encapsulation was observed and there was no evidence of any negative effect caused by the fibres. In one of the eight samples taken, a mild plasma cell reaction was observed.

Overall, the studies showed good pore structure, a thick trabeculae and fibres that are apparently well integrated with the matrix of the porous body.

Initial Surface Texture Characterisation of Samples

Surface texture characterisation has been carried out.

Samples were supplied for analysis and were subjected to characterisation using two methods:
1. White Light Scanning Interferometry—Using the Talysurf CCI 3000
   The samples were partially dried prior to measurement to enable stabilisation of their surfaces and were measured using a 20× magnification to provide an analysis area of approximately 1 mm×1 mm.
2. Atomic Force Microscopy—Using the Bruker Dimension Icon System
   The samples were fully hydrated and were measured by imaging through the fluid in peak force tapping mode.

Following the measurements, the areal surface texture parameters were calculated.

The results of the two test were as follows.

Atomic Force Micrscopy

Figure 13:
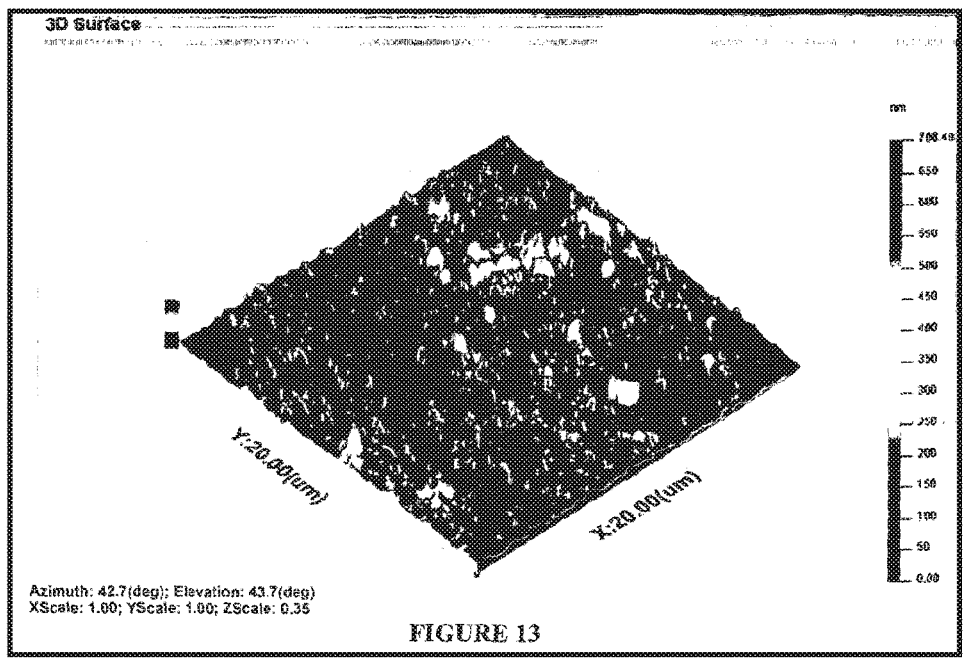
FIG. 13 is a 3d surface image of a 20 µm×20 µm sample of a device according to the invention at full hydration and using the AFM Bruker Dimension Icon System by imaging through fluid in peak force tapping mode.
Figure 14:
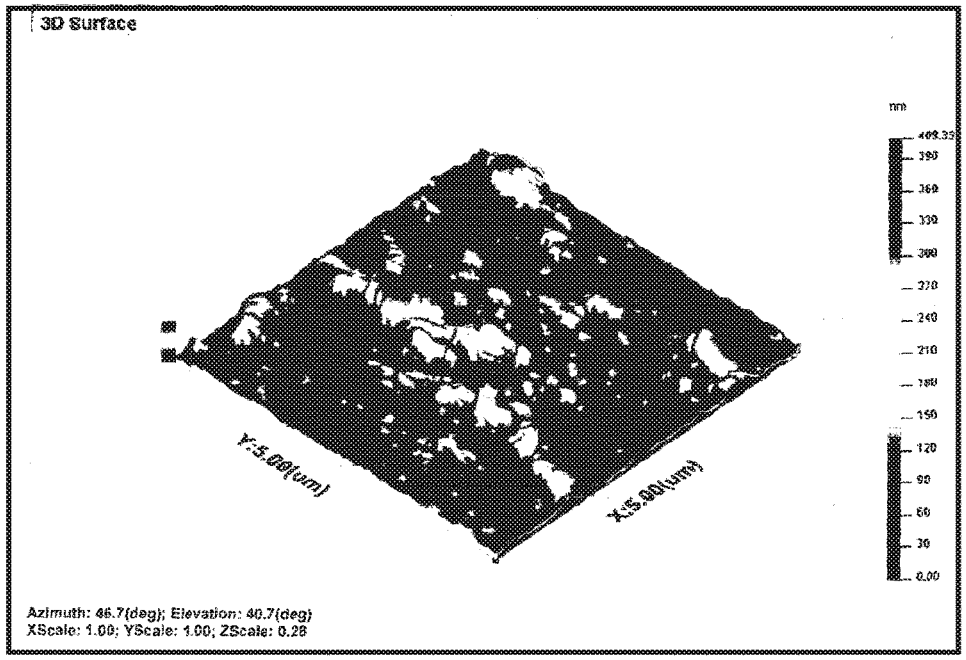
FIG. 14 is a 3d surface image of a 5 µm×5 µm sample of the device of FIG. 12 using the AFM Bruker Dimension Icon System by imaging through fluid in peak force tapping mode.

Measurements were completed on the AFM with areas of 20 μm×20 μm and 5 μm×5 μm. The images are shown in FIGS. 13 and 14, respectively.

The average surface roughness at the 20 μm×20 μm scale showed the Sa value to be 40 nm (0.04 μm) and at the 5 μm×5 μm scale, to be 32 nm (0.032 μm). The full set of results is shown in FIG. 15.

There is no definitive value for the surface roughness of articular cartilage as it is a surface which changes due to condition and use, however some studies report that features with peak to valley depth of 2.5 μm are present on the surface of most articular cartilage (Ian C Clarke (1971) "Surface Characteristics of human articular cartilage—a scanning electron microscopy study" Journal of Anatomy, v108, pp 22-30). However, BS ISO 7206 part 2 states that polymer components in articular replacement surfaces should show an average roughness of better than 2 μm Ra. Furthermore, BS ISO 7206 part 2 also states that "When measured in accordance with the principles given in ISO 468:1982, the spherical articulating surfaces of metallic and ceramic components shall have Ra values not greater than 0.05 µm and 0.02 µm respectively, using a cut-off value of 0.08 mm.".

Ra and Sa values both refer to the "average roughness" of a surface. Ra is calculated from a single profile trace and Sa is calculated over an area and so, Sa could be equated to averaging several Ra line profile traces. Sa is a more accurate descriptor for a surface as it considered data in x and y.

In any event, the average Sa value, is significantly lower than the accepted average roughness for polymer components in articular replacement surfaces and is also between the accepted values for spherical articulating surfaces of metallic and ceramic components. Therefore, the smooth surfaces are considered to be sufficiently smooth and highly advantageous for an implantable repair device.

White Light Scanning Interferometry

Figure 16:
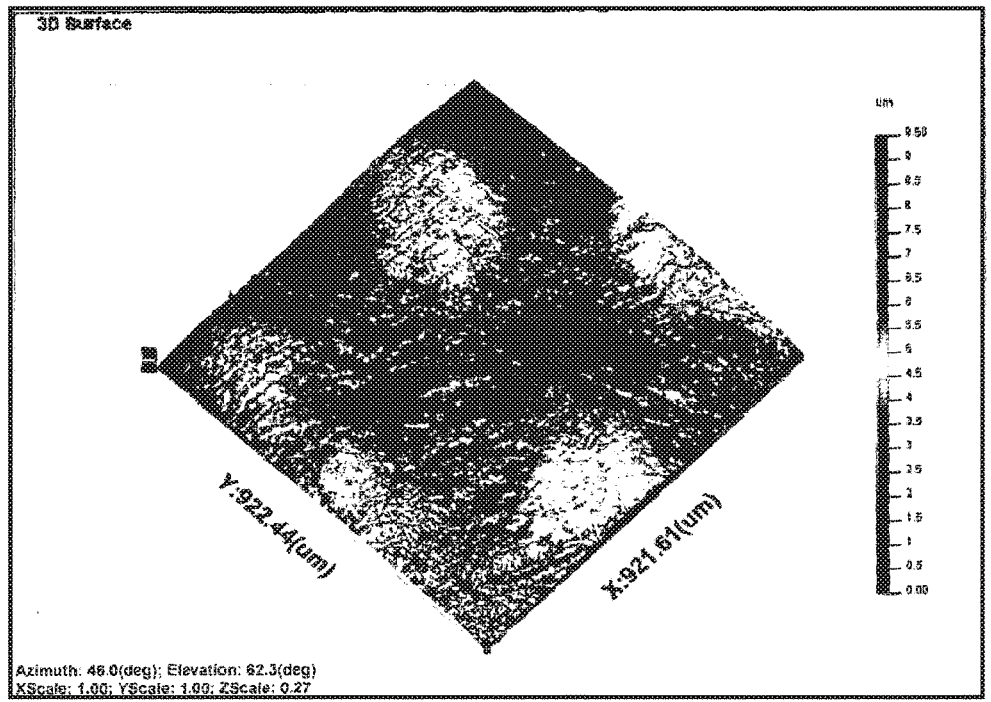
FIG. 16 shows a 3D surface map of sample of a device according to the invention in partially dried state from a white light scanning interferometer, measured using a 20× magnification, giving an area of approx. 1 mm×1 mm.
Figure 17:
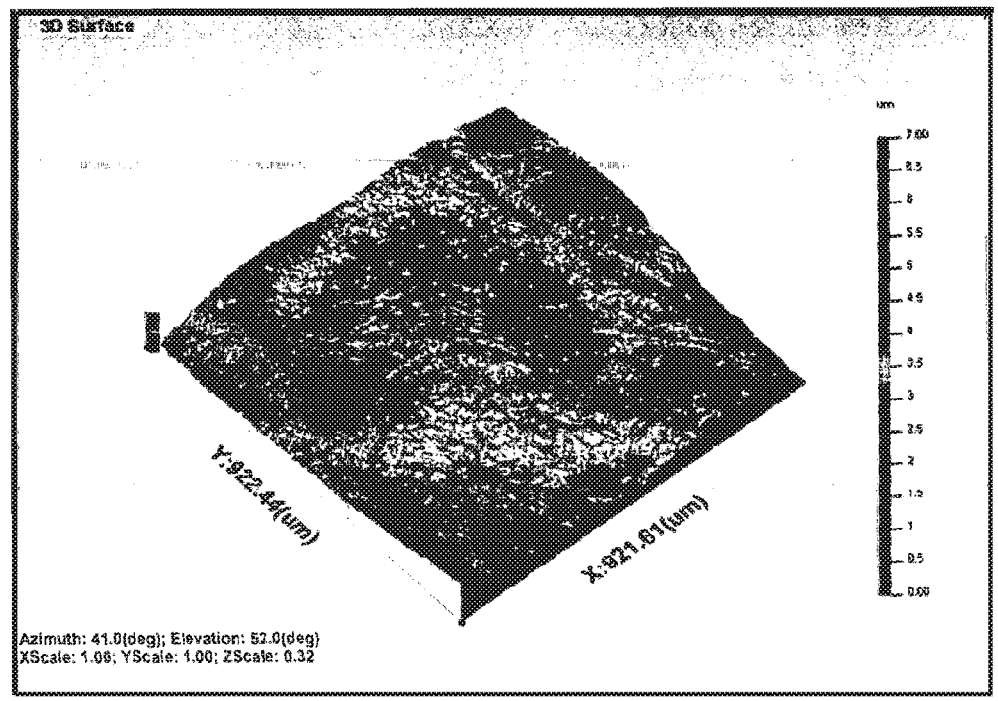
FIG. 17 shows a 3D surface map of a second sample of a device according to the invention in partially dried state from a white light scanning interferometer, measured using a 20× magnification, giving an area of approx. 1 mm×1 mm.

The images of FIGS. 16 and 17 represent 3D surface maps of the specimens from the white light scanning interferometer where the gross form has been removed from the measurements using Gaussian Polynomial fitting techniques. The resulting images therefore, show the topography of the surfaces which comprises the surface texture and the "waviness" of the surface.

Areal parameter characterisation shows that the average surface roughness across the four samples (Sa) is equal to 0.68 µm (shown in FIG. 18), with the values ranging from 0.647 to 0.709 µm.

Again, even taking into account the "waviness" of the surface, the average Sa value, is significantly lower than the accepted average roughness for polymer components in articular replacement surfaces and is therefore, highly advantageous for an implantable repair device.

Devices according to the invention have been shown to comprise a suitably smooth surface that is durable, relatively frictionless and can be lubricated to provide a wear resistant articulation surface between relatively rigid bones or adjacent tissues that exceeds the acceptable ISO 468:1982 for implantable devices of their kind. In addition, the porous surface facilitates integration with existing bone or cartilage by providing a surface for aiding ingress of cells and tissue.

Although a few preferred embodiments have been shown and described, it will be appreciated by those skilled in the art that various changes and modifications might be made without departing from the scope of the invention, as defined in the appended claims.

The invention claimed is:

1. An implantable repair device for the repair, augmentation, or replacement of tissue,
wherein the device comprises a body, the body comprising silk fibroin, the body further comprising a smooth surface, a porous surface, and porous material;
wherein the smooth surface comprises a surface of a skin on the body, the skin having a thickness from 50 µm to 300 µm; and
wherein the porous surface is formed by removing a portion of said skin from the body to thereby expose porous material thereunder, and the porous surface is provided by portions of said porous material which are at the surface of the body;
wherein the body comprises biocompatible individual fibers or a fiber lay, said biocompatible individual fibers or fiber lay being at least partially dissolved in the body of the device;
wherein the body is a single integral element comprising the porous material, the skin on the body covering a portion of the porous material and providing the smooth surface, and an exposed portion of the porous material where no skin is present, with the exposed porous material providing the porous surface.

2. The device according to claim 1, wherein the smooth surface is defined as a surface having a measured Sa value of less than approximately 0.1 µm when using Atomic Force Microscopy when samples of the repair device are fully hydrated by imaging through fluid in peak force tapping mode.

3. The device according to claim 1:
wherein the skin is between 50 µm and 300 µm thick; and
wherein the device has a thickness from 200 µm to 10,000 µm.

4. The device according to claim 1:
wherein the skin is between 50 µm and 300 µm thick; and
wherein the device has a thickness from 6 mm to 10 mm.

5. The device according to claim 1, wherein a first portion of the body comprises the skin.

6. The device according to claim 1, wherein the body comprises first and second portions, the first portion comprising at least the smooth surface and the second portion comprising at least the porous surface.

7. The device according to claim 6, wherein the first and second portions comprise discrete first and second layers, respectively that are attached to one another.

8. The device according to claim 6, wherein the second portion of the device partially or completely comprises a bone material, or an implantable bone bio-material.

9. The device according to claim 1, wherein the body comprises a regenerated silk fibroin.

10. The device according to claim 1, wherein at least a part of a second portion of the body is porous.

11. The device according to claim 1, wherein all of a second portion of the body is porous.

12. The device according to claim 10, wherein the porous part of the second portion of the body comprises open pores, and wherein the open pores form more than 70% of all pores by volume.

13. The device according to claim 1, wherein the porous surface is mineralised.

14. The device according to claim 13, wherein the porous surface is mineralised with hydroxyapatite or calcium phosphate.

15. An implantable repair device for the repair, augmentation or replacement of tissue,
wherein the implantable device comprises a body;
wherein the body comprises a skin, and wherein the skin comprises a smooth surface;
wherein the body comprises biocompatible individual fibers or a fiber lay, said biocompatible individual fibers or fiber lay being at least partially dissolved in the body of the device:
wherein the body further comprises a porous layer, the porous layer comprising a plurality of pores, and wherein the body further comprises a porous surface, the porous surface comprising a portion of the porous layer which forms a surface of the body;
the implantable repair device being prepared by a process comprising the steps of:
(A) adding a fibroin solution comprising fibroin to a mold having at least one smooth surface;
(B) at least partially gelling the fibroid solution in the mold to form a gel, the gel comprising a skin having a smooth surface;

(C) subjecting the gel to one or more freezing and thawing cycles and thereby creating pores inside the gel; and
(D) forming a porous surface on the gel by removing at least a portion of a surface of the gel to expose a portion of the porous layer inside the gel;
wherein the body of the implantable device comprises at least a portion of the gel formed by steps (A) through (D);
wherein the body is a single integral element comprising silk fibroin gel, the single integral element comprising the porous material, the skin on the body covering a portion of the porous material and providing the smooth surface, and an exposed portion of the porous material where no skin is present, the exposed porous material providing the porous surface.

16. The implantable device according to claim 15, wherein at least a portion of the porous surface is mineralized.

17. The implantable device according to claim 15:
wherein the porous layer comprises the porous surface;
wherein the pores of the porous layer of the body make up between 60% and 95% of the volume of the body;
wherein the pores of the porous layer comprise open pores, the open pores forming more than 70% of all pores by volume; and
wherein the skin is between 50 microns and 300 microns thick.

* * * * *